(12) United States Patent
Muramatsu et al.

(10) Patent No.: US 12,188,040 B2
(45) Date of Patent: Jan. 7, 2025

(54) METHOD FOR ENHANCING GENE EXPRESSION USING AAV VECTOR

(71) Applicant: GENE THERAPY RESEARCH INSTITUTION CO., LTD., Kanagawa (JP)

(72) Inventors: Shin-ichi Muramatsu, Tochigi (JP); Naomi Takino, Tochigi (JP); Mika Ito, Tochigi (JP)

(73) Assignee: GENE THERAPY RESEARCH INSTITUTION CO., LTD., Kanagawa (JP)

( * ) Notice: Subject to any disclaimer, the term of this patent is extended or adjusted under 35 U.S.C. 154(b) by 927 days.

(21) Appl. No.: 17/263,606

(22) PCT Filed: Jul. 26, 2019

(86) PCT No.: PCT/JP2019/029356
§ 371 (c)(1),
(2) Date: Jan. 27, 2021

(87) PCT Pub. No.: WO2020/026968
PCT Pub. Date: Feb. 6, 2020

(65) Prior Publication Data
US 2021/0292790 A1   Sep. 23, 2021

(30) Foreign Application Priority Data

Jul. 30, 2018   (JP) .................... 2018-142698

(51) Int. Cl.
| | |
|---|---|
| A61K 47/26 | (2006.01) |
| A61K 9/00 | (2006.01) |
| A61K 9/08 | (2006.01) |
| C12N 7/00 | (2006.01) |
| C12N 15/86 | (2006.01) |
| C12N 15/90 | (2006.01) |

(52) U.S. Cl.
CPC ............ *C12N 15/86* (2013.01); *A61K 9/0019* (2013.01); *A61K 9/08* (2013.01); *A61K 47/26* (2013.01); *C12N 7/00* (2013.01); *C12N 15/907* (2013.01); *C12N 2750/14143* (2013.01)

(58) Field of Classification Search
None
See application file for complete search history.

(56) References Cited

U.S. PATENT DOCUMENTS

2003/0138772 A1*  7/2003  Gao .................... A61P 1/04
                                              435/456

FOREIGN PATENT DOCUMENTS

| CN | 1935999 A | 3/2007 |
|---|---|---|
| JP | 2003523320 A | 8/2003 |
| JP | 2008523813 A | 7/2008 |
| JP | 2018510160 A | 4/2018 |
| WO | 9629096 A1 | 9/1996 |
| WO | 03018821 A2 | 3/2003 |
| WO | 03053476 A1 | 7/2003 |
| WO | 2007001010 A1 | 4/2007 |
| WO | 2012057363 A1 | 3/2012 |

OTHER PUBLICATIONS

Tani, K., "2. Gene Therapy in Japan"; Idenshi Igaku Mook (Genetic Medicine Mook) vol. 30; dated Jun. 20, 2016; 15 pages.
Dunbar et al.; "Gene therapy comes of age"; Science 359, 175; dated Jan. 12, 2018; 12 pages.
Choudhury SR, et al.; "Viral vectors for therapy of neurologic diseases"; Neuropharmacology doi; Nippon Rinsho vol. 75, No. 1; Dated Jan. 1, 2017; 6 pages.
Hastie et al.; "Adeno-Associated Virus at 50: A Golden Anniversary of Discovery, Research, and Gene Therapy Success—A Personal Perspective"; Human Gene Therapy 26:257-265; dated Mar. 23, 2015.
Ohmori et al.; CRISPR/Cas9-mediated genome editing via postnatal administration of AAV vector cures haemophilia B mice; Scientific Reports 17: 4159; dated Jun. 23, 2017; 11 pages.
Prakash et al.; "Two-photon optogenetic toolbox for fast inhibition, excitation and bistable modulation"; Nature Methods, vol. 9, No. 12; dated Nov. 11, 2012; 12 pages.
McCarty et al.; "Self-complementary recombinant adeno-associated virus (scAAV) vectors promote efficient transduction independently of DNA synthesis"; Gene Therapy (2001) 8; dated May 22, 2001; 7pages.
Ling et al.; "Development of Optimized AAV Serotype Vectors for High-Efficiency Transduction at Further Reduced Doses"; Human Gene Therapy Methods, vol. 27 No. 4; dated Jul. 18, 2016.
Chen et al.; "Enhancing the Utility of Adeno-Associated Virus Gene Transfer through Inducible Tissue-Specific Expression"; Human Gene Therapy Methods 24:270-278; dated Jul. 29, 2013; 9 pages.
Lida et al.; "Systemic Delivery of Tyrossine-Mutant AAV Vectors Results in Robust Transduction of Neurons in Adult Mice"; BioMed Research International, vol. 2013; dated Apr. 21, 2013; 8 pages.
International Search Report and Written Opinion dated Oct. 15, 2019, from International Application No. PCT/JP2019/029356, 13 pages.

* cited by examiner

*Primary Examiner* — Agnieszka Boesen
(74) *Attorney, Agent, or Firm* — Meunier Carlin & Curfman LLC

(57) ABSTRACT

The present invention relates to a composition for gene transfer comprising a recombinant virus vector and provides a composition for gene transfer which improves the efficiency of gene transfer using a virus vector. Specifically, the present invention provides a composition for gene transfer, which comprises a recombinant virus vector comprising a gene of interest for expression and a sugar at a concentration of at least 40 mM. The virus vector is preferably an adeno-associated virus vector. By using the composition of the present invention, the efficiency of gene transfer using a virus vector can be improved by about 50 times or more.

13 Claims, 9 Drawing Sheets

Specification includes a Sequence Listing.

[FIG. 1A]
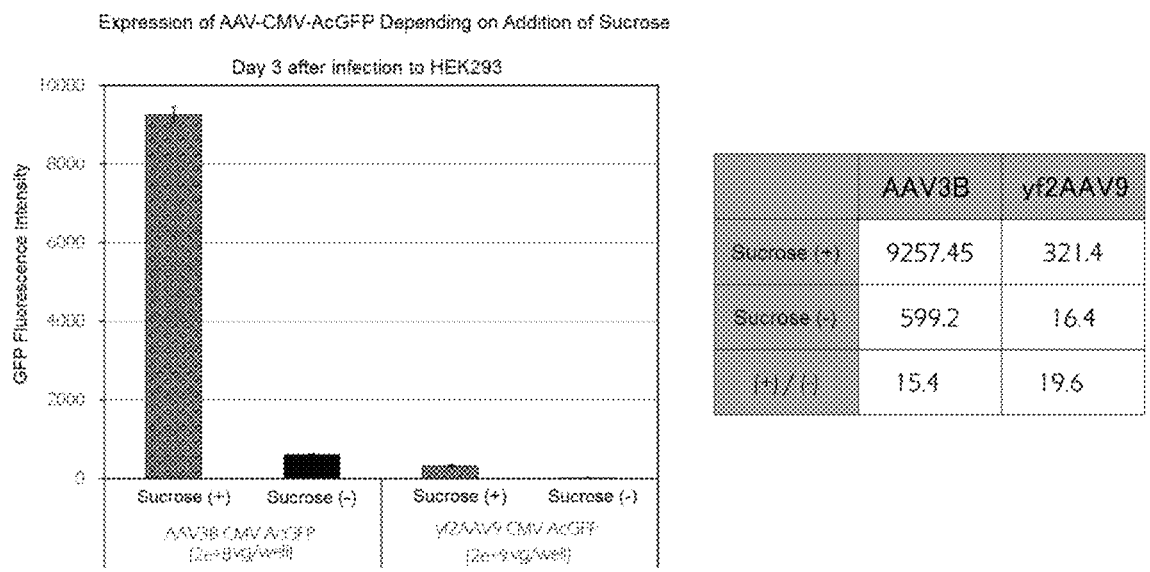
[FIG. 1B]
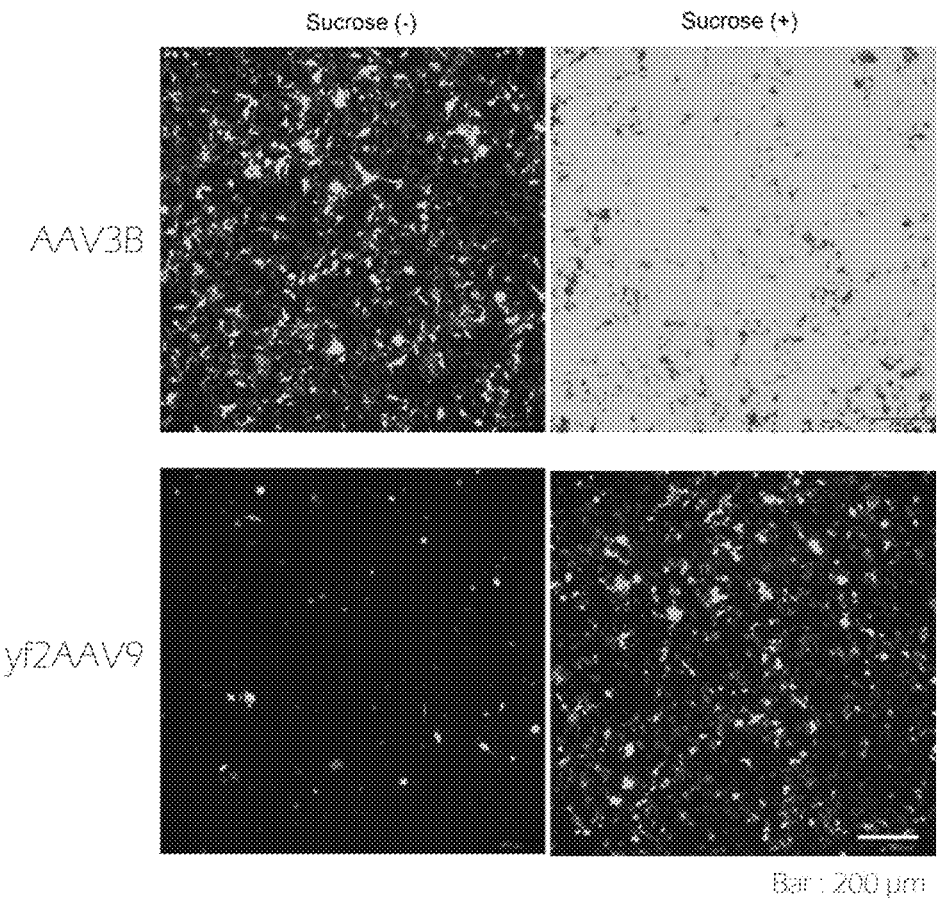

[FIG. 2A]
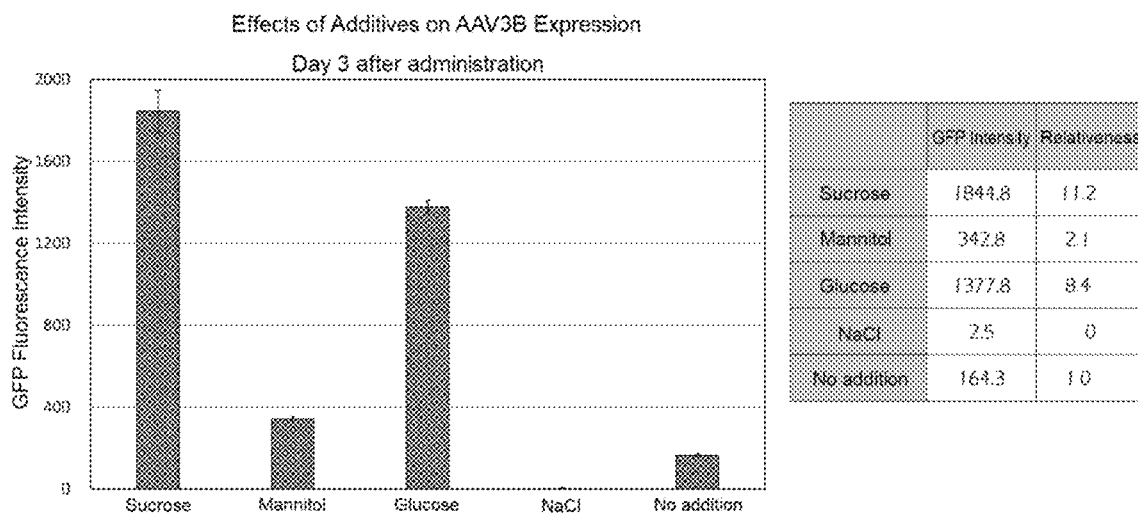
[FIG. 2B]
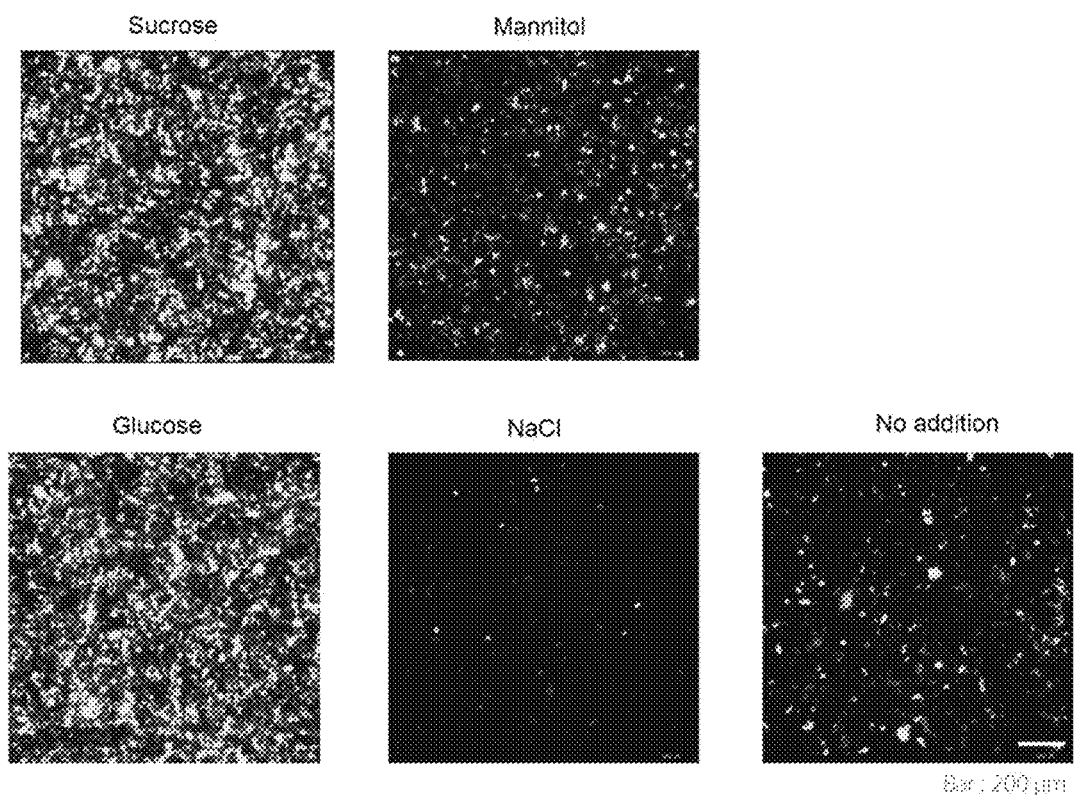

[FIG. 3]
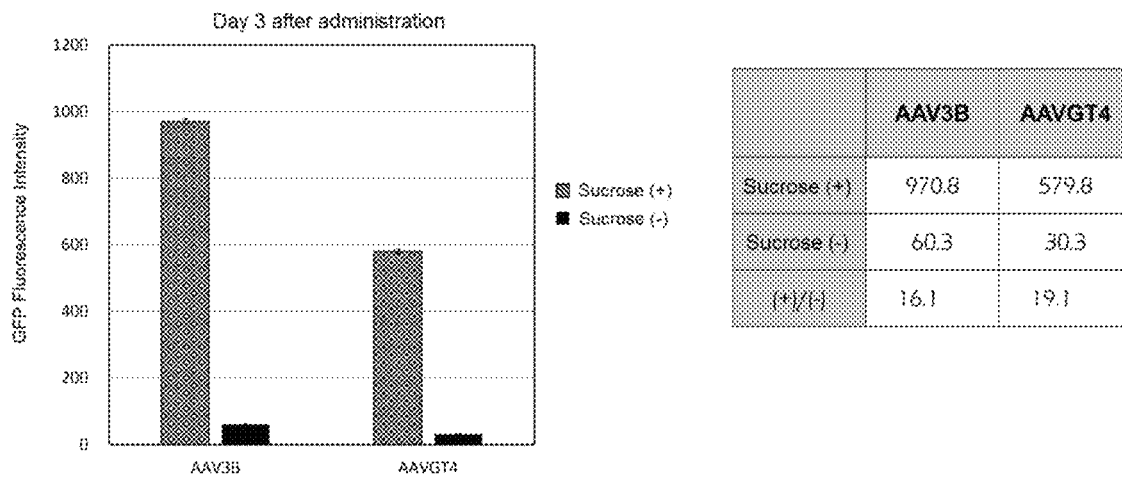
[FIG. 4A]
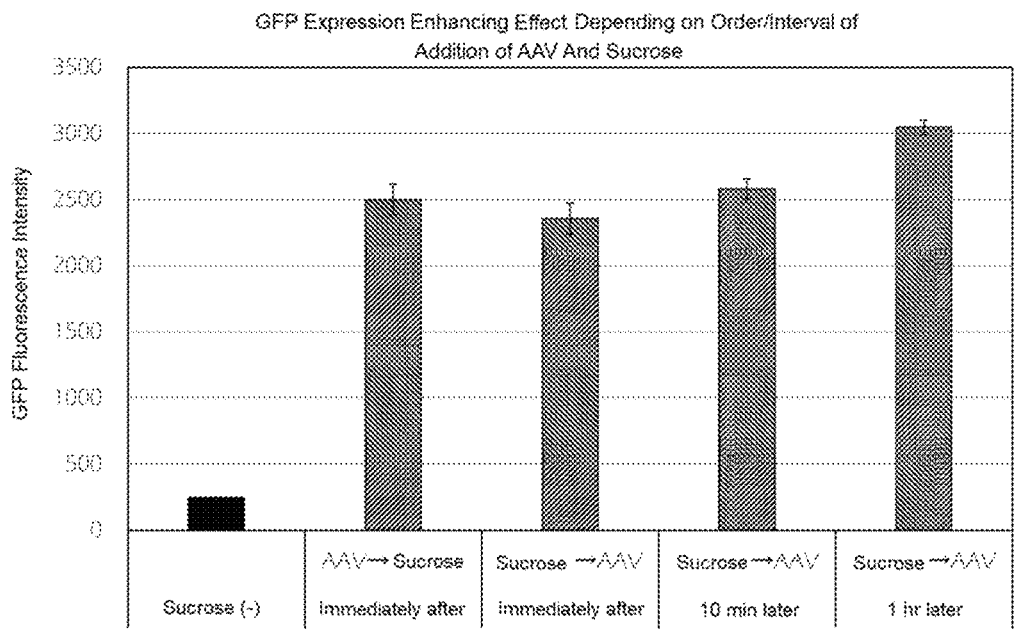

[FIG. 4B]
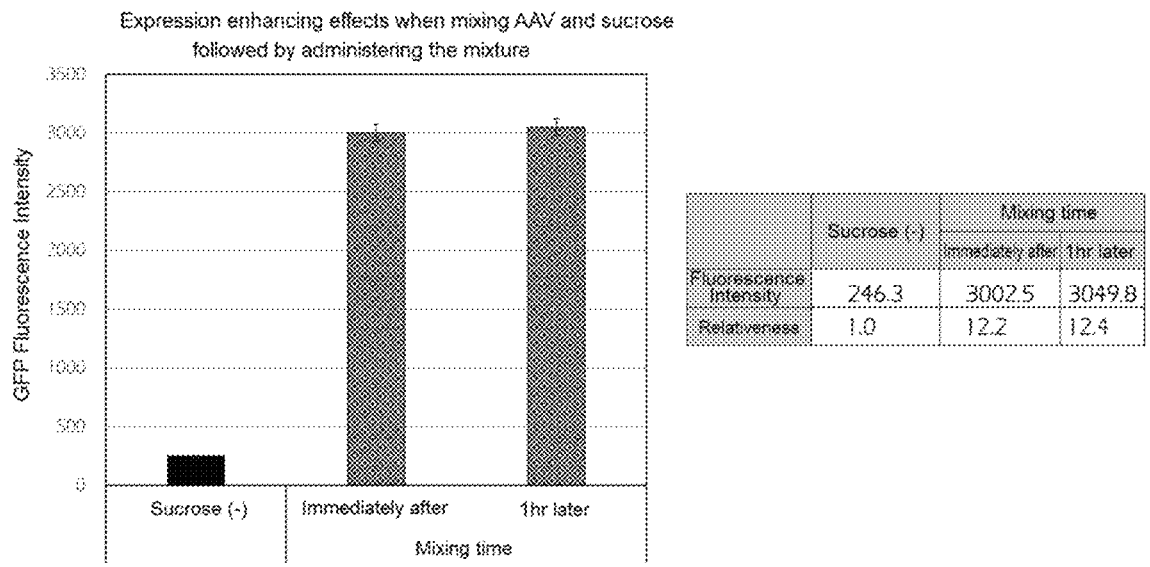
[FIG. 4C]
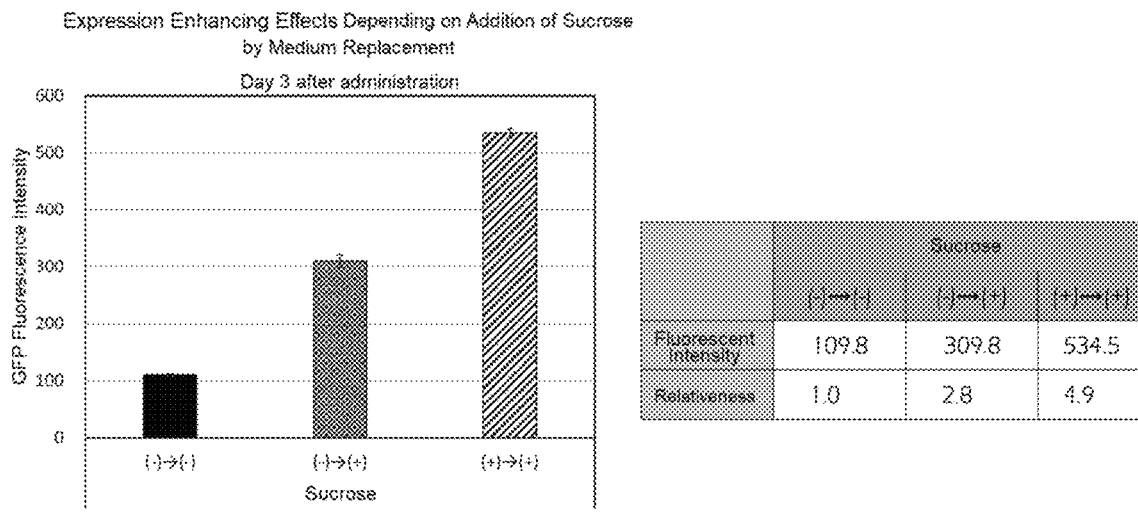

[FIG. 5A]
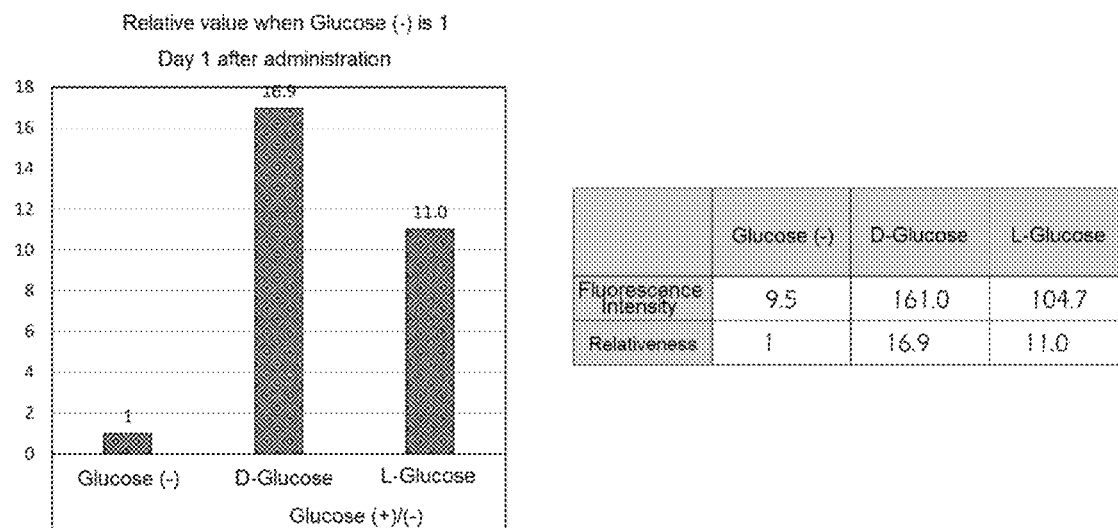
[FIG. 5B]
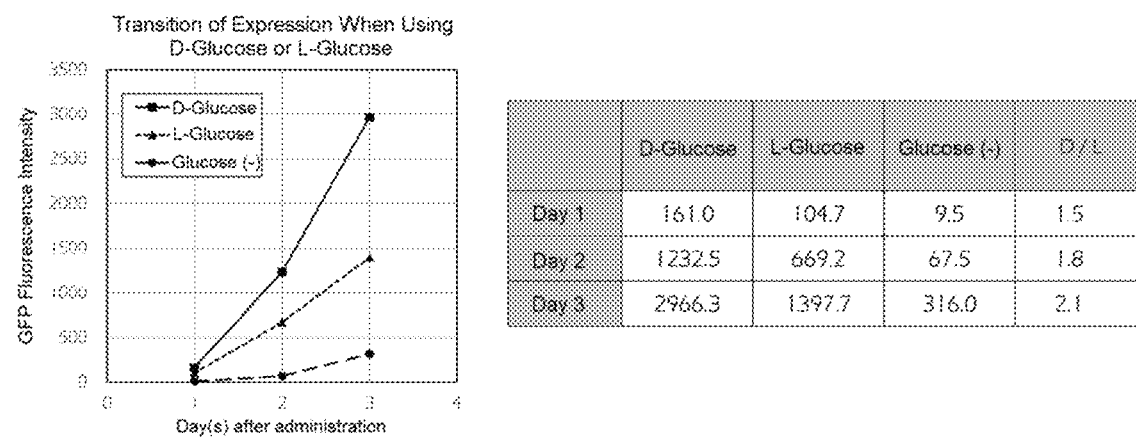

[FIG. 6]
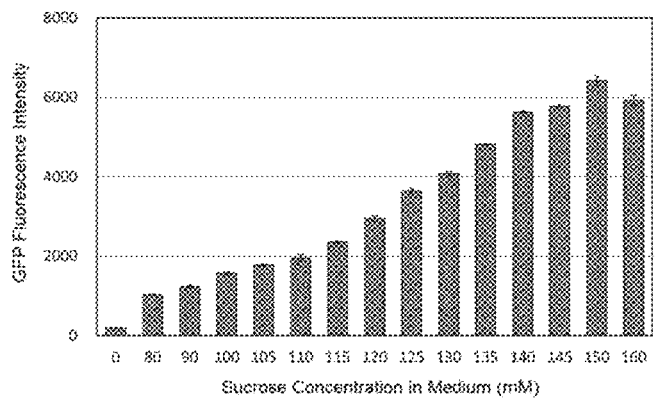
[FIG. 7]
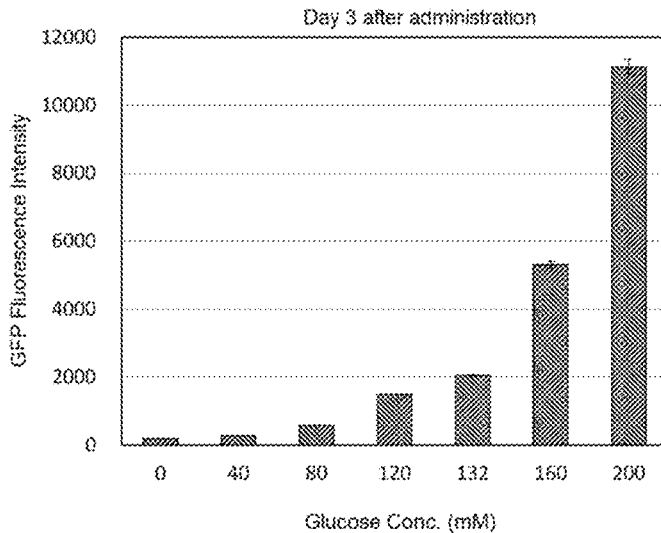

[FIG. 8A]
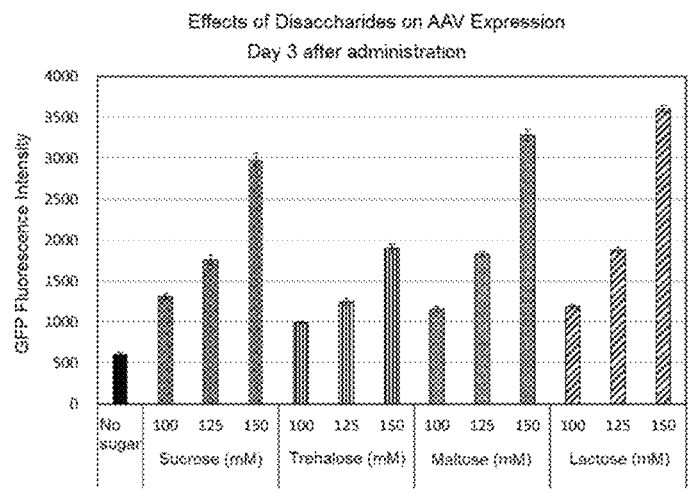
[FIG. 8B]
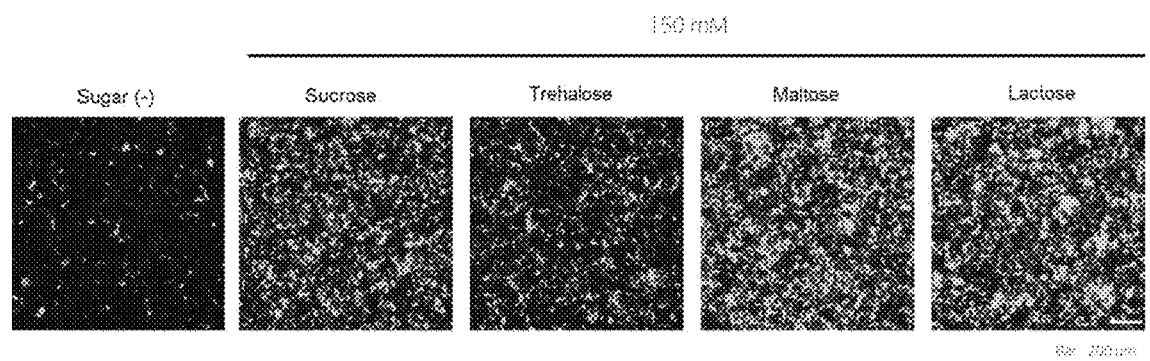

[FIG. 8C]
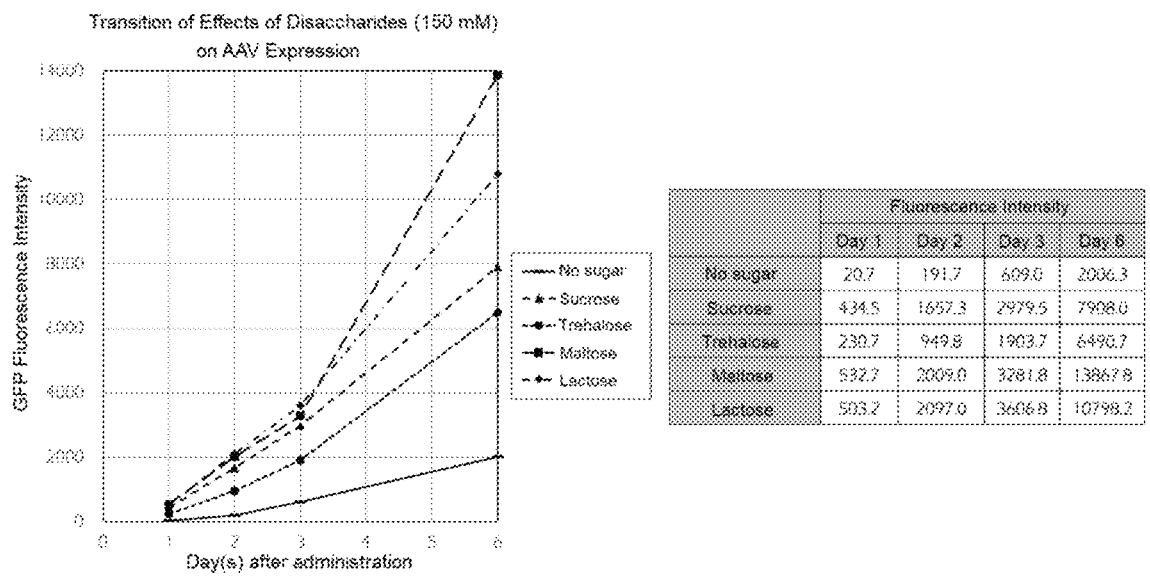
[FIG. 9A]
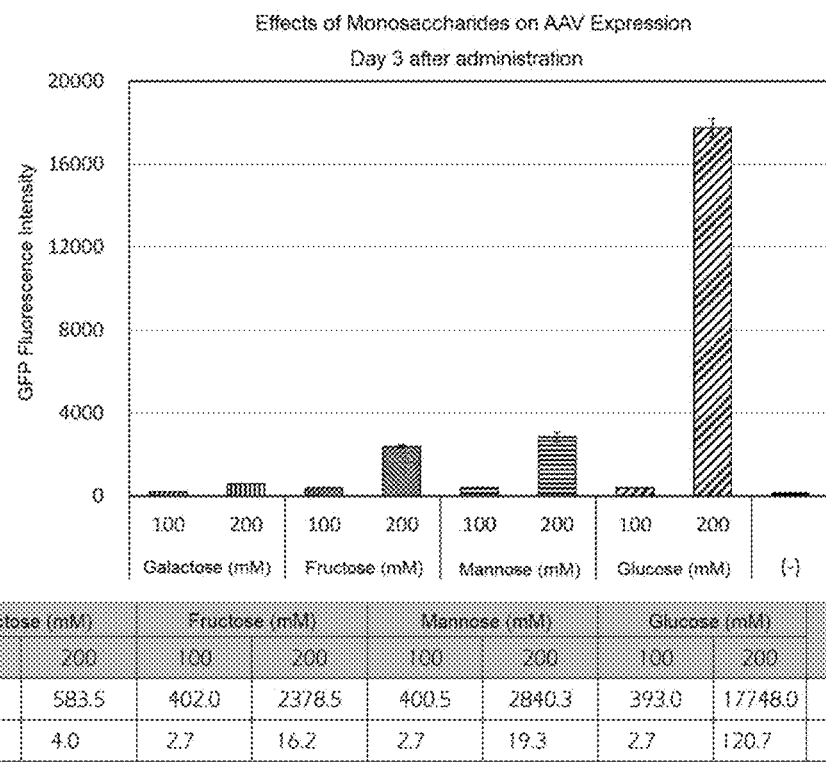

[FIG. 9B]
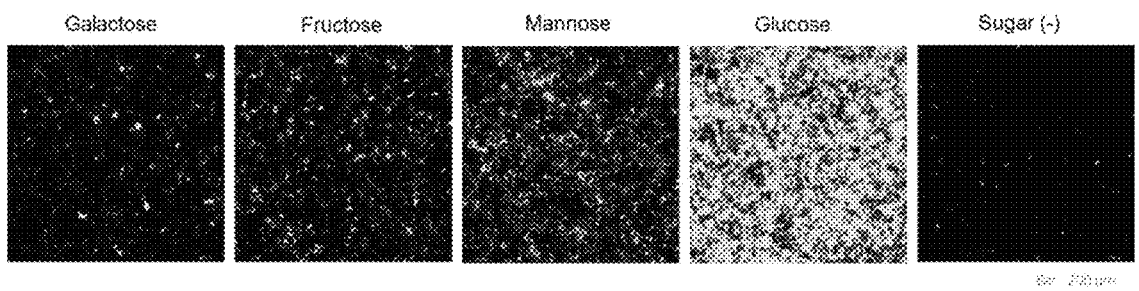

SEQUENCE LISTING

<160> NUMBER OF SEQ ID NOS: 4

<210> SEQ ID NO 1
<211> LENGTH: 736
<212> TYPE: PRT
<213> ORGANISM: adeno-associated virus 3
<220> FEATURE:
<221> NAME/KEY: MISC_FEATURE
<222> LOCATION: (1)..(736)
<223> OTHER INFORMATION: AAV3A VP1 Protein

<400> SEQUENCE: 1

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
    130                 135                 140

Ala Val Asp Gln Ser Pro Gln Glu Pro Asp Ser Ser Ser Gly Val Gly
145                 150                 155                 160
```

-continued

```
Lys Ser Gly Lys Gln Pro Ala Arg Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Ala Pro Thr Ser Leu Gly Ser Asn Thr Met Ala Ser Gly Gly Gly
        195                 200                 205
Ala Pro Met Ala Asp Asn Asn Glu Gly Ala Asp Gly Val Gly Asn Ser
210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
290                 295                 300
Gly Phe Arg Pro Lys Lys Leu Ser Phe Lys Leu Phe Asn Ile Gln Val
305                 310                 315                 320
Arg Gly Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Gln Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Asn Arg Thr
        435                 440                 445
Gln Gly Thr Thr Ser Gly Thr Thr Asn Gln Ser Arg Leu Leu Phe Ser
450                 455                 460
Gln Ala Gly Pro Gln Ser Met Ser Leu Gln Ala Arg Asn Trp Leu Pro
465                 470                 475                 480
Gly Pro Cys Tyr Arg Gln Gln Arg Leu Ser Lys Thr Ala Asn Asp Asn
                485                 490                 495
Asn Asn Ser Asn Phe Pro Trp Thr Ala Ala Ser Lys Tyr His Leu Asn
            500                 505                 510
Gly Arg Asp Ser Leu Val Asn Pro Gly Pro Ala Met Ala Ser His Lys
        515                 520                 525
Asp Asp Glu Glu Lys Phe Phe Pro Met His Gly Asn Leu Ile Phe Gly
530                 535                 540
Lys Glu Gly Thr Thr Ala Ser Asn Ala Glu Leu Asp Asn Val Met Ile
545                 550                 555                 560
Thr Asp Glu Glu Glu Ile Arg Thr Thr Asn Pro Val Ala Thr Glu Gln
                565                 570                 575
Tyr Gly Thr Val Ala Asn Asn Leu Gln Ser Ser Asn Thr Ala Pro Thr
```

```
                580               585                590
Thr Gly Thr Val Asn His Gln Gly Ala Leu Pro Gly Met Val Trp Gln
                595               600                605
Asp Arg Asp Val Tyr Leu Gln Gly Pro Ile Trp Ala Lys Ile Pro His
                610               615                620
Thr Asp Gly His Phe His Pro Ser Pro Leu Met Gly Gly Phe Gly Leu
625                 630                635                640
Lys His Pro Pro Pro Gln Ile Met Ile Lys Asn Thr Pro Val Pro Ala
                    645                650                655
Asn Pro Pro Thr Thr Phe Ser Pro Ala Lys Phe Ala Ser Phe Ile Thr
                660                665                670
Gln Tyr Ser Thr Gly Gln Val Ser Val Glu Ile Glu Trp Glu Leu Gln
                675                680                685
Lys Glu Asn Ser Lys Arg Trp Asn Pro Glu Ile Gln Tyr Thr Ser Asn
                690                695                700
Tyr Asn Lys Ser Val Asn Val Asp Phe Thr Val Asp Thr Asn Gly Val
705                 710                715                720
Tyr Ser Glu Pro Arg Pro Ile Gly Thr Arg Tyr Leu Thr Arg Asn Leu
                    725                730                735

<210> SEQ ID NO 2
<211> LENGTH: 736
<212> TYPE: PRT
<213> ORGANISM: adeno-associated virus 3
<220> FEATURE:
<221> NAME/KEY: MISC_FEATURE
<222> LOCATION: (1)..(736)
<223> OTHER INFORMATION: AAV3B VP1 protein

<400> SEQUENCE: 2

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Val Pro Gln Pro
                20                  25                  30
Lys Ala Asn Gln Gln His Gln Asp Asn Arg Arg Gly Leu Val Leu Pro
            35                  40                  45
Gly Tyr Lys Tyr Leu Gly Pro Gly Asn Gly Leu Asp Lys Gly Glu Pro
        50                  55                  60
Val Asn Glu Ala Asp Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Ile Leu Glu Pro
            115                 120                 125
Leu Gly Leu Val Glu Glu Ala Ala Lys Thr Ala Pro Gly Lys Lys Arg
        130                 135                 140
Pro Val Asp Gln Ser Pro Gln Glu Pro Asp Ser Ser Ser Gly Val Gly
145                 150                 155                 160
Lys Ser Gly Lys Gln Pro Ala Arg Lys Arg Leu Asn Phe Gly Gln Thr
                165                 170                 175
Gly Asp Ser Glu Ser Val Pro Asp Pro Gln Pro Leu Gly Glu Pro Pro
                180                 185                 190
Ala Ala Pro Thr Ser Leu Gly Ser Asn Thr Met Ala Ser Gly Gly Gly
            195                 200                 205
```

```
Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
                370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Asn Arg Thr
                435                 440                 445

Gln Gly Thr Thr Ser Gly Thr Thr Asn Gln Ser Arg Leu Leu Phe Ser
                450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
                500                 505                 510

Gly Arg Asp Ser Leu Val Asn Pro Gly Pro Ala Met Ala Ser His Lys
                515                 520                 525

Asp Asp Glu Glu Lys Phe Phe Pro Met His Gly Asn Leu Ile Phe Gly
530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
                580                 585                 590

Thr Arg Thr Val Asn Asp Gln Gly Ala Leu Pro Gly Met Val Trp Gln
                595                 600                 605

Asp Arg Asp Val Tyr Leu Gln Gly Pro Ile Trp Ala Lys Ile Pro His
610                 615                 620
```

```
Thr Asp Gly His Phe His Pro Ser Pro Leu Met Gly Gly Phe Gly Leu
625                 630                 635                 640

Lys His Pro Pro Gln Ile Met Ile Lys Asn Thr Pro Val Pro Ala
            645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
        690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 3
<211> LENGTH: 736
<212> TYPE: PRT
<213> ORGANISM: Artificial Sequence
<220> FEATURE:
<223> OTHER INFORMATION: yfAAV9 VP1 (AAV9 VP1 Y446F Y731F mutant)

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255
```

-continued

```
Tyr Lys Gln Ile Ser Asn Ser Thr Ser Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Phe Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
```

```
                675                 680                 685
Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Phe Leu Thr Arg Asn Leu
                725                 730                 735

<210> SEQ ID NO 4
<211> LENGTH: 736
<212> TYPE: PRT
<213> ORGANISM: Artificial Sequence
<220> FEATURE:
<223> OTHER INFORMATION: AAV3B mutant (S587A)

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
```

```
                305                 310                 315                 320
        Lys Glu Val Thr Gln Asn Asp Gly Thr Thr Thr Ile Ala Asn Asn Leu
                        325                 330                 335

Thr Ser Thr Val Gln Val Phe Thr Asp Ser Glu Tyr Gln Leu Pro Tyr
                        340                 345                 350

Val Leu Gly Ser Ala His Gln Gly Cys Leu Pro Pro Phe Pro Ala Asp
                        355                 360                 365

Val Phe Met Val Pro Gln Tyr Gly Tyr Leu Thr Leu Asn Asn Gly Ser
                    370                 375                 380

Gln Ala Val Gly Arg Ser Ser Phe Tyr Cys Leu Glu Tyr Phe Pro Ser
        385                 390                 395                 400

Gln Met Leu Arg Thr Gly Asn Asn Phe Gln Phe Ser Tyr Thr Phe Glu
                        405                 410                 415

Asp Val Pro Phe His Ser Ser Tyr Ala His Ser Gln Ser Leu Asp Arg
                        420                 425                 430

Leu Met Asn Pro Leu Ile Asp Gln Tyr Leu Tyr Tyr Leu Asn Arg Thr
                        435                 440                 445

Gln Gly Thr Thr Ser Gly Thr Thr Asn Gln Ser Arg Leu Leu Phe Ser
                    450                 455                 460

Gln Ala Gly Pro Gln Ser Met Ser Leu Gln Ala Arg Asn Trp Leu Pro
        465                 470                 475                 480

Gly Pro Cys Tyr Arg Gln Gln Arg Leu Ser Lys Thr Ala Asn Asp Asn
                        485                 490                 495

Asn Asn Ser Asn Phe Pro Trp Thr Ala Ala Ser Lys Tyr His Leu Asn
                        500                 505                 510

Gly Arg Asp Ser Leu Val Asn Pro Gly Pro Ala Met Ala Ser His Lys
                        515                 520                 525

Asp Asp Glu Glu Lys Phe Phe Pro Met His Gly Asn Leu Ile Phe Gly
                        530                 535                 540

Lys Glu Gly Thr Thr Ala Ser Asn Ala Glu Leu Asp Asn Val Met Ile
        545                 550                 555                 560

Thr Asp Glu Glu Glu Ile Arg Thr Thr Asn Pro Val Ala Thr Glu Gln
                        565                 570                 575

Tyr Gly Thr Val Ala Asn Asn Leu Gln Ser Ala Asn Thr Ala Pro Thr
                    580                 585                 590

Thr Arg Thr Val Asn Asp Gln Gly Ala Leu Pro Gly Met Val Trp Gln
                    595                 600                 605

Asp Arg Asp Val Tyr Leu Gln Gly Pro Ile Trp Ala Lys Ile Pro His
                    610                 615                 620

Thr Asp Gly His Phe His Pro Ser Pro Leu Met Gly Gly Phe Gly Leu
        625                 630                 635                 640

Lys His Pro Pro Pro Gln Ile Met Ile Lys Asn Thr Pro Val Pro Ala
                        645                 650                 655

Asn Pro Pro Thr Thr Phe Ser Pro Ala Lys Phe Ala Ser Phe Ile Thr
                        660                 665                 670

Gln Tyr Ser Thr Gly Gln Val Ser Val Glu Ile Glu Trp Glu Leu Gln
                        675                 680                 685

Lys Glu Asn Ser Lys Arg Trp Asn Pro Glu Ile Gln Tyr Thr Ser Asn
                        690                 695                 700
```

-continued

```
Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
            725                 730                 735
```

METHOD FOR ENHANCING GENE EXPRESSION USING AAV VECTOR

TECHNICAL FIELD

The present invention relates to a composition for gene transfer comprising a recombinant virus vector. More specifically, the present invention relates to a composition for gene transfer comprising a recombinant adeno-associated virus (rAAV) vector and a sugar.

BACKGROUND ART

Recently, virus vectors have been used to transfer exogenous genes into cells. Examples of virus vectors utilized for mammalian cells include adenovirus, adeno-associated virus, retrovirus (e.g., lentivirus) and herpesvirus vectors. These virus vectors also have been utilized and studied as virus vectors for treating diseases (Non-Patent Document 1).

Vectors for gene transfer to which an adeno-associated virus (AAV) is applied, can transfer genes into cells, including nerve cells, hepatocytes (hepatic parenchymal cells), retinal cells, muscle cells, myocardial cells, intravascular cells and adipocytes, and enable expression for a long period of time. For this reason, clinical application of such vectors as gene therapy vectors for Parkinson's disease, hemophilia, retinitis pigmentosa, etc. has been developed (Patent Documents 1-4 and Non-Patent Documents 2-4). In addition, such vectors have been frequently used as vectors for gene transfer of sgRNA and CAS9 protein in a case of gene editing and gene transferring of light-sensitive proteins such as channel rhodopsin in optogenetics (Non-Patent Documents 5 and 6). Further, for the purpose of improving transfer efficiency and gene expression, modifying genome structures, introducing a mutation or mutations to capsid proteins, replacing promoters, and others have been performed (Non-Patent Documents 7, 8 and 9). However, for example, in the case of rAAV vectors, $10^4$ vector genomes (referred to as vg, which has the same meaning as the number of copies) or more of rAAV vectors per cell is required for infection in order to achieve effective gene expression. However, inefficient infection of the vectors is often provided, and thus it is required to purify a huge amount of the vectors.

PRIOR ART DOCUMENTS

Patent Documents

Patent Document 1: International Publication WO2003/018821
Patent Document 2: International Publication WO2003/053476
Patent Document 3: International Publication WO2007/001010
Patent Document 4: International Publication WO2012/057363

Non-Patent Documents

Non-Patent Document 1: Tani, K., "2. Gene Therapy in Japan", *Idenshi Igaku* MOOK (Genetic Medicine MOOK) vol. 30, pp. 38-49, published on Jun. 20, 2016
Non-Patent Document 2: Dunber, C. E., et al.: Science 359: eaan4672, 2018
Non-Patent Document 3: Muramatsu, S., "Gene therapy for Parkinson's disease", *Nippon Rinsho* (Japanese Journal of Clinical Medicine) vol. 75: 146-150, 2017
Non-Patent Document 4: Hastie, E., Samulski, R. J.: Hum. Gene Ther. 26: 257-265, 2015
Non-Patent Document 5: Ohmori, T., et al.: Sci. Rep. 7: 4159, 2017
Non-Patent Document 6: Prakash, R., et al.: Nat. Methods 9: 1171-1179, 2012
Non-Patent Document 7: McCarty, D. M., et al.: Gene Ther. 8: 1248-1254, 2001
Non-Patent Document 8: Ling, C., et al.: Hum. Gene Ther. Methods 27: 143-149, 2016
Non-Patent Document 9: Chen, S. J., et al.: Hum. Gene Ther. Methods 24: 270-278, 2013

SUMMARY OF THE INVENTION

Problems to be Solved by the Invention

Under the above-described circumstances, it has been desired to provide a composition and means for achieving more efficient expression of gene of interest when using rAAV vectors as a recombinant virus vector.

Means for Solving the Problems

As a result of various trials and errors, the present inventors found that genes can be more efficiently transferred to various target cells (e.g., hepatocytes, nerve cells, etc.) by using a composition for gene transfer, which comprises an rAAV vector as a recombinant virus vector and a sugar at a higher concentration, and thus the present invention was achieved.

That is, the present invention provides a composition for gene transfer comprising a recombinant virus vector, a sugar, an aqueous medium, and others. Specifically, the present invention provides a composition for gene transfer, a kit and a method described below.

[1] A composition for gene transfer, which comprises a recombinant virus vector comprising a gene of interest for expression, at least 40 mM of a sugar, and an aqueous medium.

[2] The composition according to [1], wherein the recombinant virus vector is selected from the group consisting of an adeno-associated virus (AAV) vector, an adenovirus vector, a gamma-retrovirus vector and a lentivirus vector.

[3] The composition according to [1] or [2], wherein the recombinant virus vector is derived from AAV1, AAV2, AAV3, AAV4, AAV5, AAV6, AAV7, AAV8, AAV9, AAVrh10, AAVrh39, AAVrh43, AAV-B1, AAV-PHP.B or AAV-PHP.eB

[4] The composition according to any one of [1] to [3], wherein the recombinant virus vector comprises a capsid containing a protein having the amino acid sequence of SEQ ID NO: 1, 2, 3 or 4, or an amino acid sequence having at least about 90% identity to the amino acid sequence of SEQ ID NO: 1, 2, 3 or 4.

[5] The composition according to any one of [1] to [4], which comprises the sugar at a concentration of from 0.04 to 2 M.

[6] The composition according to any one of [1] to [5], wherein the sugar comprises a monosaccharide, a disaccharide or a combination thereof.

[7] The composition according to any one of [1] to [6], wherein the monosaccharide comprises at least one selected from glucose, galactose, fructose, mannose or a combination thereof.

[8] The composition according to any one of [1] to [7], wherein the monosaccharide comprises at least 60% of the D-form.

[9] The composition according to any one of [1] to [8], wherein the disaccharide comprises at least one selected from the group consisting of sucrose, trehalose, maltose, lactose and a combination thereof.

[10] The composition according to any one of [1] to [9], wherein the aqueous medium is water for injection.

[11] The composition according to any one of [1] to [10], which is a pharmaceutical in an injection or an infusion form.

[12] The composition according to any one of [1] to [11], which is an agent to be used ex vivo or in vitro.

[13] The composition according to any one of [1] to [12], which is cryopreserved and thawed prior to use.

[14] A kit for preparing the composition according to any one of [1] to [13], which comprises a recombinant virus vector and a sugar.

[15] A method for gene transfer, which comprises the steps of: (a) providing a composition comprising a recombinant virus and a sugar at a concentration of at least 40 mM; and (b) bringing the composition into contact with a culture cell in a medium comprising the sugar at a final concentration of 10 to 250 mM.

[16] A method for gene transfer, which comprises the steps of: (a) providing a composition for gene transfer, which comprises a recombinant virus, and which comprises or does not comprise a sugar; (b) bringing the composition for gene transfer into contact with a culture cell; and (c) culturing the cells in a medium comprising a sugar at a concentration of 10 to 250 mM from immediately after to 72 hours after the step (b).

[17] The method according to [15] or [16], wherein the culture cell is collected from a living subject or an established cell line.

[18] The composition for gene transfer according to any one of [1] to [13], which is for use in surgery for isolating an organ, tissue or a part thereof that is targeted for gene transfer.

Advantageous Effect of the Invention

The composition for gene transfer in the present invention, which comprises a recombinant virus vector, a sugar and an aqueous medium, can be used to transfer genes more efficiently into various target cells (e.g., hepatocytes, nerve cells, etc.). Specifically, it was demonstrated that gene expression is enhanced by about 50 times or more as compared with a control, when using a composition for gene transfer in the present invention, which comprises an AAV vector as a recombinant virus vector, a sugar at a higher concentration and an aqueous medium.

BRIEF DESCRIPTION OF THE DRAWINGS

FIG. 1A shows the results of in vitro rAAV infection in the presence or absence of sucrose. The GFP expression of the cells was measured one day after infection.

FIG. 1B shows the fluorescence microscope images of the cells relating to the experimental results of FIG. 1A.

FIG. 2A shows the results of in vitro rAAV infection in the cases of adding sucrose, mannitol or glucose.

FIG. 2B shows the fluorescence microscope images of the cells relating to the experimental results of FIG. 2A.

FIG. 3 shows the results of in vitro rAAV infection in the cases of adding sucrose.

FIG. 4A shows the results of in vitro infection immediately after, 10 minutes after, or 1 hour after mixing a virus solution with sucrose.

FIG. 4B shows the results of one day after infection in vitro immediately after or 1 hour after mixing a virus solution with sucrose.

FIG. 4C shows the results where the virus solution without sucrose was infection used for infection for 3 hours, and then the culture medium with sucrose was replaced.

FIG. 5A shows the results of in vitro rAAV infection when using D-glucose or L-glucose.

FIG. 5B shows the results at Day 1, 2 or 3 after the experiments of FIG. 5A.

FIG. 6 shows the results of in vitro rAAV infection when using sucrose at each of various concentrations.

FIG. 7 shows the results of in vitro rAAV infection when using glucose at each of various concentrations.

FIG. 8A shows the results of in vitro rAAV infection when using each of sucrose, trehalose, maltose and lactose at each of various concentrations.

FIG. 8B shows the fluorescence microscope images of the cells at Day 3 after the experiments of FIG. 8A using the concentration of 150 mM of the sugar.

FIG. 8C shows the results at Day 1, 2, 3 or 6 after the experiment of FIG. 8A.

FIG. 9A shows the results of in vitro rAAV infection when using each of galactose, fructose, mannose and glucose.

FIG. 9B shows the fluorescence microscope images of the cells at 3 days after the experiments in FIG. 9A using the concentration of 200 mM of the sugar.

MODES FOR CARRYING OUT THE INVENTION

The present invention provides a composition for gene transfer, which comprises a recombinant virus vector comprising a gene of interest for expression, a sugar at a concentration of at least 40 mM and an aqueous medium. The recombinant virus vector can be preferably selected from, but not limited to, an adeno-associated virus (AAV) vector, an adenovirus vector, a gamma-retrovirus vector and a lentivirus vector.

1. Virus Vectors Used in the Composition of the Present Invention

The recombinant virus vector used for the composition for gene transfer of the present invention (hereinafter also referred to as "the composition of the present invention") can include publicly-known virus vectors which infect to eukaryotic cells, and preferably to mammalian cells.

Examples of the virus vector which can be used for the composition of the present invention include, but are not limited to, adeno-associated virus vectors, adenovirus vectors, retrovirus vectors (including gamma-retrovirus vectors and lentivirus vectors), herpesvirus vectors, poxvirus vectors, vaccinia virus vectors, Sendai virus vectors and bornavirus vectors. The recombinant virus vector used in the present invention is preferably an adeno-associated virus vector or an adenovirus vector, and more preferably an adeno-associated virus vector.

1.1. Adeno-Associated Virus Vectors

Naturally occurring adeno-associated virus (AAV) is characterized in that it is a non-pathogenic virus and that the virus genome contained in the adeno-associated virus vector exists in the episome in the nucleus of an infected host cell for a long period of time. Utilizing these characteristics, various recombinant virus vectors are prepared to deliver genes of interest for gene therapy (for example, see: WO 2003/018821; WO 2003/053476; WO 2007/001010; *Yakugaku Zasshi* (Journal of Pharmaceutical Society of Japan), 126 (11), 1021-1028; etc.).

There are many isolated strains (serotypes) in publicly-known adeno-associated viruses (AAVs). It is publicly known that adeno-associated viruses have specificity or directivity to a target organ. Examples of adeno-associated viruses showing directivity to the liver include serotype 2, serotype 3 (including 3A and 3B) and serotype 8 (see WO2012/057363, WO2008/124724, etc.). Further, examples of adeno-associated viruses showing directivity to nerve cells include serotype 1, serotype 2, serotype 9, rh10, rh39, rh43, B-1, PHP.B and PHP.eB (for example, see Documents 10-13 below). However, an adeno-associated virus used as a therapeutic virus vector in the present invention is not limited to these isolated strains, and isolated strains and variants publicly known in the art can also be utilized.

Document 10. Sorrentino, N.C., et al.: Mol. Ther. 24: 276-286, 2016

Document 11. Choudhury, S. R., et al.: Mol. Ther. 24: 1247-1257, 2016

Document 12. Chan, K. Y., et al.: Nat. Neurosci. 20: 1172-1179, 2017

Document 13. Iida, A., et al.: Biomed. Res. Int. 2013: 974-819, 2013

A wild type AAV genome is a single-stranded DNA molecule having a full length of approximately 5 kb nucleotides, and is either a sense strain or an antisense strain. In general, the AAV genome contains inverted terminal repeat (ITR) sequences of about a 145 nucleotide length at both 5' and 3' ends of the genome. The ITR is known to have various functions, including the function as a replication origin of the AAV genome, the function as a packaging signal of the genome into a viral particle, and so on (for example, see *Yakugaku Zasshi* (Journal of Pharmaceutical Society of Japan) 126 (11), 1021-1028, etc.). The internal region of the wild type AAV genome flanked by the ITRs (hereinafter referred to as the internal region) contains an AAV replication (rep) gene and a capsid (cap) gene. The rep gene and the cap gene encode, respectively, a protein Rep involved in virus replication and a capsid protein capable of forming a capsomere (e.g., at least one of VP1, VP2 and VP3) which is an outer shell of the regular icosahedral structure. For further details, it is possible to reference to, e.g., Human Gene Therapy, 13, pp. 345-354, 2002, Neuronal Development 45, pp. 92-103, 2001, *Jikken Igaku* (Experimental Medicine), 20, pp. 1296-1300, 2002, *Yakugaku Zasshi* (Journal of the Pharmaceutical Society of Japan), 126 (11), 1021-1028, Hum. Gene. Ther., 16, 541-550, 2005, etc.

The rAAV vector used in the present invention is a vector derived from naturally occurring adeno-associated virus serotype 1 (AAV1), serotype 2 (AAV2), serotype 3 (AAV3a/AAV3b), serotype 4 (AAV4), serotype 5 (AAV5), serotype 6 (AAV6), serotype 7 (AAV7), serotype 8 (AAV8), serotype 9 (AAV9) or serotype rh10 (rhAAV10: Hu, C., et al., Molecular Therapy Vol. 22, No. 10, October 2014, 1792-1802), but not limited thereto. The nucleotide sequences of the adeno-associated virus genomes are publicly known and designated as the GenBank accession numbers of AF063497.1 (AAV1), AF043303 (AAV2), NC 001729 (AAV3), U48704 (AAV3A), AF028705.1 (AAV3B), NC 001829.1 (AAV4), NC 006152.1 (AAV5), AF028704.1 (AAV6), NC 006260.1 (AAV7), NC 006261.1 (AAV8), AY530579.1 (AAV9), AY631965 (AAV10), etc., respectively.

In the present invention, the protein included in the recombinant virus vector is a protein having the amino acid sequence of SEQ ID NO: 1, 2, 3 or 4, or an amino acid sequence having at least 80%, and preferably at least 85%, at least about 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to the amino acid sequence of SEQ ID NO: 1, 2, 3 or 4, and the protein forms a virus vector or a capsid (outer shell) of a virus vector under physiological conditions.

1.2. Adenovirus Vectors

It can be said that a vector for gene therapy using adenovirus (hereinafter also referred to as a "recombinant adenovirus vector") is one vector that has been most frequently used in pharmaceutical clinical trials (see Japanese National-phase PCT Laid-Open Patent Publication No. H08-501686, Japanese National-phase PCT Laid-Open Patent Publication No. H10-506542, Non-Patent Document 1, and Documents 14 and 15 below). As a recombinant adenovirus vector already put into practical use, a recombinant adenovirus vector incorporated with a human tumor suppressor gene, p53, was approved as a gene therapy agent for the first time in the world in 2003 and has been commercially available as "Gendicin" (trade name). It is publicly known that recombinant adenovirus vectors have a wide scope of host cells (animal species, cell species, etc. to be targeted). Further, an adenovirus gene is not incorporated into the chromosome and exists independently in the nucleus of a target cell, and thereby a recombinant adenovirus vector can transiently express a gene of interest. Specifically, when a recombinant adenovirus vector is administered to a living subject, expression of a gene of interest can usually disappear after 1 to 2 weeks. Example disadvantages of recombinant adenovirus vectors include high immunogenicity in living subjects.

Document 14. Yokoda, R. T., et al.: Biomedicines 6: 33, 2018

Document 15. Zhang, C. and Zhou, D.: Hum. Vaccin. Immunother. 12: 2064-2074, 2016

An adenovirus genome is a linear double-stranded DNA molecule having a length of about 36 kb, and encodes at least about 30 genes, including early genes and late structural genes required for virus replication. Further, an outer shell of an adenovirus is in a form where a capsid made of capsid proteins is exposed, and this point is similar to an outer shell of an adeno-associated virus.

The early genes of an adenovirus can be categorized into 4 regions located in the adenovirus genome (E1 to E4: E represents "early"). The regions include 6 transcription units and have promoters of themselves. The late genes (L1 to L5: L represents "late") partially overlaps with initial transcription units and almost of the portions are transcribed under a major late promoter (MLP).

For further details regarding recombinant virus vectors utilizing adenovirus, it is possible to reference, for example, Documents 14 and 15 above.

1.3. Retrovirus Vectors

As used herein, it is intended that the retrovirus vectors encompass gamma-retrovirus vectors (or an oncovirus vector) and lentivirus vectors. Examples of the gamma-retrovirus vectors include a vector derived from Moloney murine leukemia virus (MoMLV). Examples of the lentivirus vectors include vectors derived from human immunodeficiency virus type 1 (HIV 1) and vectors derived from simian immunodeficiency virus (SIV).

Retrovirus vectors can be used to incorporate a polynucleotide of interest for transduction into the chromosome of a target cell with high efficiency, and to express the polynucleotide of interest permanently. Meanwhile, since retrovirus vectors are originally derived from a virus causing a disease such as leukemia and immunodeficiency syndrome, it is noticed that a malignant neoplasm or the like may be provided by retrovirus vectors. A gene size capable of being incorporated may include, for example, 9 kb or less (Toi, et al., Virus (in Japanese), Vol. 65, No. 1, pp. 27-36, 2015; Vargas, J. E., et al.: J. Transl. Med. 14: 288, 2016; Poletti, V. and Mavilio, F.: Mol. Ther. Methods Clin. Dev. 8: 31-41, 2017).

A retrovirus has envelope proteins and envelope membrane as an outer shell of the virus. Many retroviruses have RNA genomes, and examples of the genes encoded by the genome include: a gag/pol gene, which encodes a precursor protein forming a viral structural protein, a protease, a reverse transcriptase, an integrase and the like; and an env gene, which encodes an envelope glycoprotein. Both the ends of the virus genome are flanked by LTRs (long terminal repeats), and the LTRs include an enhancer, a promoter, a polyadenylation signal, and others.

For details on the other characteristics, properties, etc. of retrovirus vectors, it is possible to reference, for example, Mann, et al., Cell 33: 153-159 (1983); Cone and Mulligan, Proc. Natl. Acad. Sci. USA 81: 6349-6353 (1984); Vargas, J. E., et al.: J. Transl. Med. 14: 288, 2016; Poletti, V and Mavilio, F.: Mol. Ther. Methods Clin. Dev. 8: 31-41, 2017.

1.4. Genes of Interest for Expression

The recombinant virus vector used in the present invention may include a gene (polynucleotide) of interest for expression which is introduced into a target cell in the recombinant virus genome and is contained in the virus vector. Examples of such genes of interest for expression to be introduced include, but are not limited to, a gene having a sequence which is functional as a gene itself, a gene having a sequence whose transcript is functional, a gene which has a sequence translated into a protein to exert a function, and a combination thereof. That is, the gene of interest for expression contained in the recombinant virus vector used in the present invention is not particularly limited as long as the recombinant virus vector can carry the gene, in view of the size of the gene and the like.

Regarding the gene of interest for expression contained in the recombinant virus vector used in the present invention, examples of the sequence which is functional as a gene itself include a promoter sequence, a telomere sequence, a polyadenylation signal sequence and a sequence binding a protein of interest.

Examples of the sequence, which is contained in the recombinant vector used in the present invention and whose transcript is functional, include, but are not limited to, a polynucleotide that alters (e.g., destroys or diminishes) a function of a targeted endogenous gene, such as an antisense molecule, ribozyme, interfering RNA (iRNA) or microRNA (miRNA), and a polynucleotide that alters (e.g., down-regulates) an expression level of an endogenous protein. Methods for producing or using a double-stranded RNA (dsRNA, siRNA, shRNA or miRNA) have been known with reference to many publications (see, e.g., Japanese National-phase PCT Laid-Open Patent Publication No. 2002-516062; US 2002/086356A; and Nature Genetics, 24(2), 180-183, 2000 February).

Examples of the sequence, which is contained in the recombinant vector used in the present invention and to be translated into a protein, include sequences encoding a growth factor, a trophic factor, a cytokine, an antigen, an antibody, a tumor suppressor, a metabolic enzyme, a suicide gene, a receptor, a transporter, a growth inhibitor, and a protein for genome editing or repairing, and a combination thereof. In addition, an expression cassette which contains a reporter gene known in the art, such as green fluorescent protein (GFP), may be also used.

The recombinant virus vector used in the present invention may include a plurality of vectors containing the above-described gene of interest for expression. Further, in the recombinant virus vector to be used in the present invention, a plurality of genes of interest for expression may be contained in a single vector.

Examples of the gene of interest for expression, which is introduced by the recombinant virus vector of the present invention, include, but are not limited to, hepatocyte growth factor (HGF), nerve cell growth factor (NGF), hemoglobin, interleukin-1, interleukin-2, interleukin-3, interleukin-4, interleukin-5, interleukin-6, interleukin-7, interleukin-8, interleukin-9, interleukin-10, interleukin-11, GM-CSF, G-CSF, M-CSF, human growth factor, insulin, factor VIII, factor IX, tPA, LDL receptor, tumor necrosis factor (TNF), PDGF, EGF, NGF, IL-1ra, EPO, $\beta$-globin, and an enzyme for cleaving a specific site or sites on genome (e.g., TALEN, CRISPR and ZFN). The polynucleotide of interest which is introduced by the recombinant virus vector of the present invention may be derived from either a different species or the same species relative to a cell, tissue or patient to be targeted.

The promoter sequence which can be used in the present invention is not particularly limited, as long as the above-described gene of interest for expression can be expressed in a target cell.

For example, versatile promoters derived from mammals or viruses can be used in the present invention. Examples of such promoters include, but are not limited to, a PGK promoter, an EF1-$\alpha$ promoter, a $\beta$-globin promoter, a CMV promoter, an SV40 promoter, an MMLV-LTR promoter and an HIV-LTR promoter.

Further, a promoter specific to a target cell can be used in the present invention. In the case where a target cell is a neuronal cell, examples of the promoter include, but are not limited to, a synapsin I promoter sequence, a myelin basic protein promoter sequence, a neuron-specific enolase promoter sequence, a calcium/calmodulin-dependent protein kinase II (CMKII) promoter sequence, a tubulin $\alpha$I promoter sequence, a platelet-derived growth factor $\beta$-chain promoter sequence, a glial fibrillary acidic protein (GFAP) promoter sequence, an L7 promoter (cerebellar Purkinje cell specific promoter) sequence, a glial fibrillary acidic protein (hGfa2) promoter sequence, a glutamate receptor delta 2 promoter (cerebellar Purkinje cell specific promoter) sequence, and a glutamic acid decarboxylase (GAD65/GAD67) promoter sequence.

In the present invention, in the case where a target cell is a hepatocyte, examples the promoter include, but are not limited to, an ApoE promoter, an antitrypsin promoter, a cKit promoter, promoters of liver-specific transcription factors (HNF-1, HNF-2, HNF-3, HNF-6, C/ERP, DBP), an albumin promoter, a thyroxine binding globulin (TBG) promoter, and a synthetic promoter (e.g., HCRhAAT promoter, as described in, for example, WO2018/131551).

These promoter sequences may be appropriately modified to be used in the present invention as long as the promoter functions are retained in a target cell.

1.5. Target Diseases

Examples of therapeutic methods which comprises using the composition of the present invention as a pharmaceutical include gene therapy, cancer virotherapy and virus immunotherapy. Gene therapy has been studied in the art in relation to, for example, congenital genetic diseases, diseases caused by functional deterioration with aging. Cancer virotherapy has been studied in relation to, for example, viruses targeting cancer cells to induce lysis, apoptosis, etc. Virus immunotherapy has been studied in relation to, for example, therapeutic methods which comprises using a virus for inducing an immune response that is advantageous for treating a target disease, such as CART therapy.

Examples of target diseases in the therapy using a virus vector specifically include congenital genetic diseases, such as adenosine aminase deficiency (ADA-SCID), X-linked severe combined immunodeficiency (X-SCID), chronic granulomatous disease (CGD), β thalassemia, Leber congenital amaurosis (LCA) and adrenoleukodystrophy (ALD). Examples of cancers targeted by cancer virotherapy include lung cancer, kidney cancer, prostate cancer, esophageal cancer, brain tumor and melanoma. Examples of other diseases include arteriosclerosis obliterans, angina, myocardial infarction, Alzheimer's disease, Parkinson's disease, ALS, HIV, hepatitis, age-related macular degeneration, diabetes and rheumatoid arthritis, and have been studied (for example, see: Non-Patent Document 1; Non-Patent Document 2; and Piguet, F., et al.: Hum. Gene Ther. 28: 988-1003, 2017).

2. Sugars

The composition of the present invention is characterized by comprising a sugar together with the above-described recombinant virus vector. As used herein, the "sugar" may be referred to as "sugars".

Examples of the sugar used in the composition of the present invention include a sugar publicly known to be available in the field of pharmaceutical products. Preferably, examples of the sugar used in the present invention include a sugar available for injections or infusions. Examples of the sugar include a monosaccharide (such as a triose, a tetrose, a pentose and a hexose) and a disaccharide.

Preferred examples of the sugar used in the composition of the present invention include, but are not limited to, erythrose, threose, ribose, arabinose, xylose, lyxose, allose, altrose, glucose, mannose, gulose, idose, galactose, talose, erythrulose, ribulose, xylulose, psicose, fructose, sorbose, tagatose, sucrose, trehalose, maltose, lactose, and a combination thereof.

The sugar used in the composition of the present invention may include a stereoisomer. For example, the structure of each sugar (monosaccharide) contained in the composition of the present invention may take the D-form, the L-form, and a combination thereof. Preferably, at least about 60%, at least 70%, at least 80%, at least 90%, or at least 95% of the monosaccharide contained in the composition of the present invention may have the D-form.

The monosaccharide used in the composition of the present invention may take a cyclic structure or a linear structure. Examples of the cyclic structure include a pyranose type with a 6-membered ring and a furanose type with a 5-membered ring. The cyclic structure may take the α-form or the β-form depending on the conformation of the hydroxyl group bonded to the carbon atom at position 1 (C1). The monosaccharide used in the composition of the present invention may take any of the α-form, the β-form and a mixture thereof. Unless otherwise indicated, the cyclic structure of the monosaccharide as described herein includes the α-form, the β-form and/or a mixture thereof.

Further, the composition of the present invention may comprise sugar alcohol which is commonly known in the art and available for a pharmaceutical product. Preferred examples of the sugar alcohol include, but are not limited to, erythritol, xylitol, sorbitol, mannitol and a combination thereof.

The composition of the present invention may comprise a modified sugar which is commonly known in the art and available for a pharmaceutical product. Examples of the modifications for obtaining such a modified sugar include, but are not limited to, publicly-known modifications applied to pharmaceutical products, such as acetylation, N-acetylglucosamination, N-acetylgalactosamination, sialylation, glucuronidation, iduronidation, phosphorylation, sulfation and ribosylation. Preferred examples of the modifications to a sugar which are used in the composition of the present invention include, but are not limited to, N-acetylglucosamination, N-acetylgalactosamination, sialylation, glucuronidation, iduronidation and a combination thereof.

The composition of the present invention may be in the form of an aqueous solution comprising a sugar at a concentration of at least 40 mM. The concentration of 40 mM corresponds to about 0.7% aqueous solution in the case of the monosaccharide and about 1.4% aqueous solution in the case of the disaccharide. For example, in the range of the sugar concentration in the composition of the present invention, the lower limit is 40 mM or more of glucose, 80 mM or more of sucrose, 40 mM or more of trehalose, 40 mM or more of maltose, or 40 mM or more of lactose, and the upper limits is the saturated concentration of the monosaccharide or disaccharide in the composition, or 240 mM or less of glucose, 200 mM or less of sucrose, 200 mM or less of trehalose, 200 mM or less of maltose, or 200 mM or less of lactose (with the proviso that a combination should satisfy the lower limit <the upper limit). For example, the composition of the present invention may comprise the monosaccharide or disaccharide, specifically, glucose at the concentration of 200 mM, sucrose at the concentration of 160 mM, trehalose at the concentration of 160 mM, maltose at the concentration of 160 mM, or lactose at the concentration of 160 mM.

Two or more of the above-described sugars may be used in combination. Examples of the combinations include a combination of glucose and sucrose, a combination of sucrose and maltose, a combination of glucose, sucrose and maltose, and a combination of sucrose and maltose. Sugar concentrations preferable for introduction of a gene of interest may be used, including, for example, a concentration at which each of the sugars is in the range of from a lower limit to an upper limit, and a concentration where a total concentration of the respective sugars is in the range of from an upper limit to a lower limit for one of the sugars.

In general, in the case of basal culture media used for culturing eukaryotic cells, particularly mammalian cells, a sugar concentration should be in the range of from 1 to 4.5 g/L. The concentration corresponds to from about 6 to 25 mM in terms of glucose. When using the composition of the present invention for ex vivo or in vitro gene transfer, the final concentration of the sugar may be, for example, from 40 to 240 mM of glucose, from 80 to 200 mM of sucrose, from 40 to 200 mM of trehalose, from 40 to 200 mM of maltose, or from 40 to 200 mM of lactose. As described above, two or more of these sugars may be used in combination.

Regarding the composition of the present invention, the final sugar concentration for ex vivo or in vitro gene transfer can be appropriately calculated depending on the amount of a culture medium to be used.

Regarding the blood sugar level in a living subject, in terms of normal humans, a lower limit is from 80 to 100 mg/dL (e.g., between meals or at the time of fasting), and an upper limit is from 150 to 160 mg/dL (e.g., after a meal). Accordingly, the blood sugar level is considered to fall within a narrow range of 5.0 to 8.5 mM. When using the composition of the present invention, the final concentration of each sugar in vivo can be adjusted to be 10 mM or less. As described above, two or more of the sugars may be used in combination.

Regarding the composition of the present invention, the final concentration of the sugar in the case of in vivo gene transfer can be calculated on the basis of, for example, the body weight, water content and/or blood volume of a target patient to be administrated, or volume, blood and tissue fluid (e.g., cerebrospinal fluid) of a target tissue for gene transfer. In calculation of an example case for a human adult with the body weight of 60 kg, publicly-known amounts, such as the water content of about 60% and the blood volume of about 8% (about 5 L), can be used.

Optionally, it is possible to use an operative method for the purpose of increasing the local concentration of the recombinant virus vector and the sugar in the composition for gene transfer of the present invention. For example, a specific organ, tissue or a part thereof targeted for gene transfer can be separated from a living subject and brought into temporal contact with the sugar at a higher concentration. More specifically, the blood flow, lymph, cerebrospinal fluid or others in a site targeted for gene transfer (e.g., an organ, tissue or a part thereof) is temporarily stopped (separated) using a clamp or others, and substitution, perfusion and/or flushing are carried out with a pharmaceutically available aqueous medium (e.g., physiological saline), and then the composition of the present invention can be administered to the flushed site. As a specific example of such an operation, a method in which portal vein blood in the liver is temporarily flushed using a physiological saline and then an AAV vector is administered thereto is known (Mimuro, et al., Molecular Therapy Vol. 21, No. 2, February 2013, 318-323). Example of the final concentration of the sugar in this case includes, for example, but is not limited to, a concentration of from 50 to 100 mM, from 60 to 90 mM, or from 70 to 80 mM.

Moreover, when using the composition of the present invention for intrathecal administration, in view of an amount of cerebrospinal fluid (e.g., about 150 mL for an adult), a final concentration higher than the blood concentration may be used. Example of the final concentration of the sugar in this case includes, but is not limited to, a concentration of from 50 to 100 mM, from 60 to 90 mM, or from 70 to 80 mM.

The sugar contained in the composition of the present invention may be combined at a desired concentration with the recombinant virus vector at a period of immediately prior to use (usually 5 minutes or less) to one day before use, for example, 10 minutes before use, 20 minutes before use, 30 minutes before use, 1 hour before use, 2 hours before use, 3 hours before use, 4 hours before use, 5 hours before use, 6 hours before use, 12 hours before use (or one night before use), or one day before use. In the case where the composition of the present invention is prepared before use as described above, the sugar concentration in the composition of the present invention may be adjusted to be, for example, 40 to 240 mM of glucose, 80 to 200 mM or sucrose, 40 to 200 mM of trehalose, 40 to 200 mM of maltose, or 40 to 200 mM of lactose. These concentrations may be used in view of the above-described final concentrations.

Further, the composition of the present invention may be provided in the form of a concentrate and diluted before use (e.g., immediately prior to use (5 minutes or less before use), 10 minutes before use, 20 minutes before use, 30 minutes before use, etc.).

Alternatively, the composition of the present invention may be cryopreserved in a state where the sugar is contained at the above-described concentration. When cryopreserved, the composition may be in the form of a concentrate but does not have to be in the form of a concentrate. When the composition of the present invention is cryopreserved, preferably, it can be preserved for a period of 1 month or less, 2 months, 3 months, 6 months, 1 year, 2 years, 5 years, 10 years or longer. After that, the composition is thawed before use (e.g., immediately prior to use (5 minutes or less before use), 10 minutes before use, 20 minutes before use, 30 minutes before use, one night before use), and optionally diluted to a desired concentration.

The step of bringing a target cell or tissue into contact with the composition of the present invention may be carried out temporarily. For example, contacting a target cell, tissue or organ with the composition of the present invention can be carried out at a culture temperature (or a temperature lower than the culture temperature such as the ambient temperature) for a certain period of time, for example, for a period of 30 minutes to several days (7 days), more specifically, for 1 hour, for 1.5 hours, for 2 hours, for 2.5 hours, for 3 hours, for 6 hours, for 12 hours (overnight), for 18 hours, for 24 hours (1 day), for 2 days, or others. Then, the target cell, tissue or organ may be replaced by a fresh medium without the composition of the present invention, or newly and repeatedly contacted with the composition of the present invention.

During the above procedure, it is possible to use the sugar and the final concentration thereof as described above, which includes, for example, 40 to 240 mM of glucose, 80 to 200 mM of sucrose, 40 to 200 mM of trehalose, 40 to 200 mM of maltose, and 40 to 200 mM of lactose (e.g., final concentration in a medium) for ex vivo or in vitro procedures, and 10 mM of the monosaccharide or disaccharide (e.g., in blood) for in vivo procedures.

When the composition of the present invention is administered, for example, in vivo, an administration period can be set to be shorter than usual in the art, and thereby suffering to patients can be reduced.

3. Other Characteristics of the Composition of the Present Invention 3.1. Preparation at the Time of Use The composition of the present invention comprises a sugar at a predetermined concentration. When the composition is actually used as a pharmaceutical composition, it is supposed that the sugar to be administered is sometimes desired to be limited or reduced depending on a health condition of a patient. In this case, the composition of the present invention can be prepared before use and at the time of use.

In one embodiment, the composition of the present invention may be provided in a form of solution containing a sugar at a predetermined concentration. In another embodiment, the composition of the present invention may be provided in a form for preparation at the time of use. Such a form may be, for example, a kit including a vial or ampule containing the recombinant virus vector, and a vial or ampule containing the sugar. The vector and the sugar in each vial or ampule may be in the form of aqueous solution or in a dried form by means of freeze-drying or the like. Moreover, the kit of the present invention may further include solution for dissolving the recombinant virus vector and the sugar (aqueous medium such as water for injection). Furthermore, the kit of the present invention is packaged with instruction sheet provided by a manufacturer.

When the composition of the present invention is prepared at the time of use, it can be prepared immediately prior to use (5 minutes or less before use) to 12 hours before use (one night before use), for example, 10 minutes before use, 20 minutes before use, 30 minutes before use, 1 hour before use, 2 hours before use, 3 hours before use, 6 hours before use, or 12 hours before use (one night before use).

Further, the composition of the present invention may be provided in the form of a concentrate and diluted before use (e.g., immediately prior to use (5 minutes or less before use) to 12 hours before use (a night before use), for example, 10 minutes before use, 20 minutes before use, 30 minutes before use, etc.).

Alternatively, the composition of the present invention may be cryopreserved in a state where the sugar at the above-described concentration is present or not contained, for example, for 1 month or less, 2 months, 3 months, 6 months, 1 year, 2 years, 5 years, 10 years or a period of time longer than that, and thawed before use (e.g., immediately prior to use (5 minutes or less before use), 10 minutes before use, 20 minutes before use, 30 minutes before use, etc.), and optionally diluted in a manner such that the sugar at a desired final concentration is contained in the composition.

The temperature for preparation as described above may be a temperature equal to or lower than a culture temperature, for example, an ambient temperature (room temperature), or may be a low temperature at which the solution of the composition of the present invention is not frozen.

3.2. Use In Vivo, Ex Vivo or In Vitro

The composition of the present invention can be brought into contact with culture cells. Examples of such cells include, but are not limited to, established culture cells and primary cells collected from a living subject. Cells in which a gene of interest is introduced by the composition of the present invention can be utilized for intended use such as therapies and studies.

The composition of the present invention may be used either in vitro or ex vivo, and may also be used in vivo. Preferably, the composition of the present invention is a pharmaceutical composition, and may be used at the time of culturing cells removed from a living subject to be returned thereto or may be directly administered to a living subject. Further, the composition of the present invention may be in the form of a reagent comprising, for example, a recombinant virus vector having a reporter gene.

The composition of the present invention may be administered as a pharmaceutical composition to a living subject (in vivo). For example, adeno-associated viruses have an advantage in that the viruses have cell tropism to various target tissues depending on isolated strains (serotypes). In this case, the composition prepared in advance to have a desired sugar concentration can be administered to a living subject using a dosage form such as an injection and an infusion.

Further, the composition of the present invention can be administered via publicly-known administration routes such as peripheral administration, intramuscular administration, intraportal administration, intrathecal administration and intracerebral administration.

Moreover, the composition of the present invention can be used for surgery for separating an organ, tissue or a part thereof targeted for gene transfer. In such surgery, in order to elevate the local concentration of the recombinant virus vector and the sugar in the composition of the present invention, the blood flow, lymph, cerebrospinal fluid or the like of a site targeted for gene transfer (e.g., an organ, tissue, and a part of an organ or tissue) is temporarily separated using a clamp or others, and then substitution, perfusion and flushing with a pharmaceutically available aqueous medium (e.g., physiological saline) are carried out. After that, the composition for gene transfer of the present invention can be administered to the separated site. As a specific example thereof, a method is known in which portal vein blood in the liver is temporarily flushed using a physiological saline and then an AAV vector is administered thereto (see Mimuro, et al., Molecular Therapy Vol. 21, No. 2, February 2013, 318-323).

3.3. Dosage Form of Pharmaceutical Composition

When the composition of the present invention is used as a pharmaceutical composition, the composition may be administered, e.g., orally, parenterally (intravenously), through cerebrospinal fluid, intramuscularly, through the oral mucosa, rectally, intravaginally, subcutaneously, intranasally, by inhalation, etc., preferably, parenterally, and more preferably, intravenously. The active ingredient in the pharmaceutical composition of the present invention may be formulated solely or in combination, and may also be provided as a pharmaceutical preparation by formulation with a pharmaceutically acceptable carrier or an additive for a pharmaceutical preparation. In these cases, the active ingredient of the present invention may be contained in the pharmaceutical preparation in an amount of, for example, 0.1 to 20 wt %, and preferably 1 to 5 wt % in the composition.

The active ingredient in the pharmaceutical composition of the present invention may be formulated alone or in combination, and may also be provided as a pharmaceutical preparation by formulation with a pharmaceutically acceptable carrier or an additive for a pharmaceutical preparation. In these cases, the active ingredient of the present invention may be contained in the pharmaceutical preparation in an amount of, for example, 0.1 to 20 wt %, and preferably 1 to 5 wt % in the composition. Examples of the pharmaceutically acceptable carrier or additive that can be used include a diluent, a dissolution agent, a dissolution aid, an isotonic agent, a pH regulator, a stabilizer and a dye.

Examples of the pharmaceutical preparations suitable to parenteral administration can include injections, infusions, suppositories, etc. For parenteral administration, the components including the recombinant virus vector and the sugar used in the pharmaceutical composition of the present invention may be dissolved in an aqueous medium (purified water, sterile purified water, water for injection, physiological saline or the like), sesame oil or peanut oil, or in aqueous propylene glycol solution, and a resultant solution can be used for the administration. The aqueous solutions should be appropriately buffered (preferably pH 8 or higher) as necessary, and be isotonic liquid diluent in first. For example, physiological saline can be used as such a liquid diluent. The prepared aqueous solutions are suitable for intravenous injection, and, in contrast, the oily solutions are suitable for intra-articular injection, intra-muscular injection and subcutaneous injection. The preparation of all these solutions under sterile conditions can be readily accomplished by standard pharmaceutical techniques well known to those skilled in the art.

Examples of the pharmaceutical preparations suitable for oral administration can include liquids, and syrups. In the case of oral administration, preferred preparations may contain, for example, lactose (milk sugar) or high molecular weight polyethylene glycols. When aqueous suspensions and/or elixirs are desired for oral administration, the active ingredient may be used in combination with various sweeteners or corrigents, coloring agents or dyes, and, if necessary, emulsifying and/or suspending agents as well, together with diluents such as water, ethanol, propylene glycol, glycerin, and combinations thereof.

The dose of the pharmaceutical composition of the present invention is not particularly limited, and an appropriate dose can be chosen depending on various conditions such as type of disease, age and symptoms of the patient, administration route, therapeutic goal, presence or absence of concurrent drugs, etc. The dose of the pharmaceutical composition of the present invention is, but not limited to, for example, 1 to 5,000 mg, and preferably 10 to 1,000 mg per day for an adult (e.g., body weight of 60 kg). The composition of such daily dose may be administered daily in 2 to 4 divided doses. For example, when vg (vector genome) is used as a dosage unit, the dose may be chosen, but not limited to, in the range of, for example, from $10^9$ to $10^{14}$ vg, preferably, $10^{10}$ to $10^{13}$ vg, and more preferably, $10^{10}$ to $10^{12}$ vg per body weight of 1 kg. Further, regarding the above-described dose, the unit or amount may be changed depending on the virus to be used. As such a dose, a publicly-known amount generally used in the art can be used for the composition of the present invention.

3.4. Reagent and Kit of the Present Invention

The composition of the present invention may be in the form of a reagent to be used ex vivo or in vitro for cultured cells. In this case, an aqueous medium for the composition of the present invention may be a basal medium or concentrated medium, in addition to the above-described aqueous medium such as water for injection and physiological saline. Moreover, the recombinant virus vector of the present invention may contain a publicly-known reporter gene such as GFP. Such a marker can be used, for example, for selecting a gene-transferred cell ex vivo or in vitro, and for validating conditions of gene transfer in vivo.

The composition of the present invention may be provided in the form of a kit for preparing the composition. In the kit (also referred to as the kit of the present invention), the recombinant virus vector used in the present invention may comprise, for example, an empty vector DNA to be packaged in the recombinant virus vector, a helper virus, a helper virus DNA or the like. More specifically, for example, in the case of a rAAV vector, the first polynucleotide is a DNA polynucleotide for incorporation of a gene (polynucleotide) of interest for expression, and the second polynucleotide is a DNA polynucleotide encoding a helper virus (e.g., AdV helper). Further, the kit of the present invention may further have an instruction sheet provided by a manufacturer, which describes a procedure for preparing the recombinant virus vector using the kit of the present invention.

4. Other Terms as Used Herein

The meanings indicated by the terms as used herein are as described below. Terms not particularly described herein are intended to refer to meanings commonly understood by persons skilled in the art.

As used herein, the terms "virus or viral vector", "virus virion" and "virus or viral particles" are interchangeably used, unless otherwise indicated. Further, the term "virus or viral vector" refers to a vector prepared by gene recombination even if it is not particularly specified.

As used herein, the term "polynucleotide" is interchangeably used with "nucleic acid," "gene" or "nucleic acid molecule," which is intended to mean a nucleotide polymer. As used herein, the term "nucleotide sequence" is used interchangeably with "nucleic acid sequence" or "base sequence," which is represented by a sequence of deoxyribonucleotides (abbreviated as A, G, C, and T).

The "virus or viral genome" according to the present invention may be in the form of either a DNA (e.g., cDNA or genomic DNA) or an RNA (e.g., mRNA) unless otherwise specified. The viral genome as used herein may be a double-stranded or a single-stranded DNA or RNA. Such a single-stranded DNA or RNA may be either a coding strand (i.e., a sense strand) or a non-coding strand (i.e., an anti-sense strand).

Regarding the explanation herein for placing a promoter, a gene of interest, polyadenylation signal, etc. on the gene, which are encoded by the rAAV genome, if the rAAV genome is a sense strand, the strand itself is referred to and if it is an antisense strand, its complementary strand is referred to, unless otherwise specified. Further, in the description, "r" that represents recombination may be omitted when it is clear from the context.

As used herein, the terms "protein" and "polypeptide" are interchangeably used and intended to mean a polymer of amino acids. The polypeptide as used herein is represented in accordance with conventional peptide designation, in which the N-terminus (amino terminus) is on the left hand and the C-terminus (carboxyl terminus) on the right hand. A partial peptide in the polypeptide of the present invention (as used herein, may be briefly referred to as a partial peptide of the present invention) includes a partial peptide of the polypeptide of the present invention described above, preferably having the same properties as the above polypeptide of the present invention has.

As used herein, the term "plasmid" refers to various known gene elements, for example, a plasmid, a phage, a transposon, a cosmid, a chromosome, etc. The plasmid can be replicated in a particular host and transport gene sequences between cells. As used herein, the plasmid contains various known nucleotides (DNA, RNA, PNA and a mixture thereof) and may be a single strand or a double strand, and preferably a double strand. As used herein, the term "rAAV vector plasmid" is intended to include a double strand formed by rAAV vector genome and its complementary strand, unless otherwise specified. The plasmid used in the present invention may be linear or circular.

Terms not particularly described herein are intended to refer to meanings commonly understood by persons skilled in the art.

Examples

Hereinafter, the present invention is described in more detail by referring to Examples, but the scope of the present invention should not be limited to the following Examples.

A. Materials and Methods
(a) GFP Expression AAV Vector

Three types of AAV vectors (AAV3B, yf2AAV9 and AAVGT4) were used. In yf2AAV9, the tyrosine (Y) residues at positions 446 and 731 in capsid protein VP1 of AAV9 were substituted with phenylalanine (F) residues (Iida et al., BioMed Research International, Vol. 2013, Article ID 974819). In AAVGT4, the serine (S) residue at position 587 in VP1 of AAV3B was substituted with alanine (A) residue (SEQ ID NO: 4). In each AAV vector, an expression cassette composed of cytomegalovirus (CMV) promoter, a cDNA of green fluorescent protein (AcGFP) and an SV40 poly(A) was inserted between the inverted terminal repeats (ITR) of publicly-known AAV3A.

AAV3A: GenBank Accession #U48704 (the amino acid sequence of VP1 protein is represented by SEQ ID NO: 1)
AAV3B: GenBank Accession #AF028705.1 (the amino acid sequence of VP1 protein is represented by SEQ ID NO: 2)
AAV9: GenBank Accession #AY530579.1
yf2AAV9: (the amino acid sequence of VP1 protein is represented by SEQ ID NO: 3)
AAVGT4: (The amino acid sequence of VP1 protein is represented by SEQ ID NO: 4)

(b) Cell Culturing
1) HEK 293 cells
HEK293 cells ($5\times10^4$/well) were seeded and maintained in 10% fetal calf serum (FCS)-DMEM/F12 medium under 5% $CO_2$ at 37° C.
2) HepG2 cells
HepG2 cells ($5\times10^4$/well) were seeded and maintained in 10% FCS DMEM low glucose medium (Thermo Scientific) under 5% $CO_2$ at 37° C.

(c) Sugars
Monosaccharides: glucose, galactose, fructose, and mannose
Disaccharides: sucrose, trehalose, maltose, and lactose
Sugars were added to a culture medium in a manner such that the final concentrations as described below were obtained.
Glucose: 0 to 200 mM
The other monosaccharides: 100 mM, 200 mM
Sucrose: 0 to 187 mM
The other disaccharides: 100 mM, 125 mM, 150 mM (d) Infection with Virus Vectors
To the culture cells of (b) above, $6\times10^7$ to $5\times10^8$ vg/well of AAV3B-CMV-AcGFP expressing GFP described in Item (a) above was added, or $2\times10^9$ vg/well of yf2AAV9-CMV-AcGFP was added, and then the cells were cultured for 3 to 6 days.

(e) Evaluation of GFP Expression
The fluorescence intensity of GFP was measured using a plate reader (BioTek Japan) and comparison thereof was made. Further, the images of typical view fields were taken using the fluorescence microscope (Olympus IX83).

EXPERIMENTAL RESULTS AND DISCUSSION

Experiment 1: Effects of Sucrose on Infection/Expression of AAV

On a 96 well Optical bottom plate (ThermoFisher), $5\times10^4$ cells/well of HEK293 cells were seeded, and the next day, either $2\times10^8$ vg/well of AAV3B-CMV-AcGFP or $2\times10^9$ vg/well of yf2AAV9-CMV-AcGFP was added thereto. Subsequently, sucrose (Wako) was added thereto in a manner such that the final concentration thereof in the medium became 125 mM. Specifically, 1.25 M sucrose solution dissolved in the medium was added in such a manner as the amount of the solution reached 1/10 of the total amount of the medium. To a sucrose (−) control, the same amount of the medium as that of the sucrose solution was added. After cell cultivation for 3 days under 5% $CO_2$ at 37° C. in an incubator, the fluorescence intensity of GFP was measured using the plate reader (BioTek Japan) and comparison thereof was made (FIG. 1A). Further, the images of typical view fields were taken using the fluorescence microscope (Olympus IX83) (FIG. 1B).

As the results of the experiments, GFP expression was increased 15.4 times in the case of AAV3B and 19.6 times in the case of yf2AAV9 due to the addition of sucrose (represented by (+)).

TABLE 1

| | AAV3B | yf2AAV9 |
|---|---|---|
| Sucrose (+) | 9257.45 | 321.4 |
| Sucrose (−) | 599.2 | 16.4 |
| (+)/(−) | 15.4 | 19.6 |

Experiment 2: Presence or Absence of Expression Increasing Effect when Using Sucrose, Mannitol, Glucose or NaCl On a 96 well Optical bottom plate, $5\times10^4$ cells/well of HEK293 cells were seeded and $6\times10^7$ vg/well of AAV3B-CMV-AcGFP was added to the medium on the next day. Subsequently, 125 mM of sucrose, or glucose (Sigma), mannitol (NIHON PHARMACEUTICAL CO., LTD.) or NaCl (Wako) was added to the medium so as to provide the osmotic pressure equal to that of 125 mM sucrose. The final concentrations thereof were 125.0 mM, 132.3 mM, 132.3 mM and 71.5 mM, respectively. The medium in the same amount as that of the additive solution was added to provide a control. After cell cultivation for 3 days under 5% $CO_2$ at 37° C. in an incubator, the fluorescence intensity of GFP was measured using the plate reader and comparison thereof was made (FIG. 2A). Further, the images of typical view fields were taken using the fluorescence microscope (Olympus IX83) (FIG. 2B).

As the results of the experiments, due to the addition of sucrose, glucose or mannitol, the expression was increased by 11 times, 8 times or twice, respectively. When NaCl was added, expression was remarkably reduced.

TABLE 2

| | GFP intensity | Relativeness |
|---|---|---|
| Sucrose | 1844.8 | 11.2 |
| Mannitol | 342.8 | 2.1 |
| Glucose | 1377.8 | 8.4 |
| NaCl | 2.5 | 0 |
| No Additive | 164.3 | 1.0 |

Experiment 3: Expression Increasing Effects in HepG2 Cells

On a 96 well Optical bottom plate, $5\times10^4$ cells/well of HepG2 cells were seeded, and $5\times10^8$ vg/well of AAVGT4-CMV-AcGFP or $5\times10^8$ vg/well of AAV3B-CMV-AcGFP was added to the medium on the next day. Subsequently, sucrose was added thereto in such a manner as the final concentration thereof in the medium reached 125 mM. To a sucrose (−) control, the medium in the same amount as that of the sucrose solution was added. After cell cultivation for 3 days under 5% $CO_2$ at 37° C. in an incubator, the fluorescence intensity of GFP was measured using the plate reader and comparison thereof was made.

As the results of the experiments, in HepG2 cells, a cell line derived from human liver cancer, expression was also increased by 16.1 times in the case of AAV3B and 19.1 times in the case of AAVGT4 by the addition of sucrose.

TABLE 3

|  | AAV3B | AAVGT4 |
|---|---|---|
| Sucrose (+) | 970.8 | 579.8 |
| Sucrose (−) | 60.3 | 30.3 |
| (+)/(−) | 16.1 | 19.1 |

Experiment 4: Expression Enhancing Effects when Using Sucrose with Various Adding Methods On a 96 well Optical bottom plate, $5×10^4$ cells/well of HEK293 cells were seeded and AAV vectors in combination with sucrose were administered on the next day by using various adding methods. In each of the cases, after cell cultivation for 3 days in an incubator under 5% $CO_2$ at 37° C., the fluorescence intensity of GFP was measured using the plate reader and comparison thereof was made. In each case, the AAV vector was AAV3B-CMV-AcGFP at $1×10^8$ vg/well and the final concentration of sucrose was 125 mM.

As the first procedure, 4 methods of the addition were carried out, including adding sucrose immediately (5 minutes or less) after the administration of the AAV vector, and the administration of the AAV vector immediately (5 minutes or less) after, 10 minutes after or 1 hour after adding sucrose to cells. To a control sucrose (−), the medium in the same amount as that of the sucrose solution was added.

In the sucrose-added group, expression was increased by about 10 times even when any of the adding methods was carried out (FIG. 4A).

TABLE 4A

|  | Sucrose(−) | Immediately AAV => Sucrose | Immediately Sucrose => AAV | 10 min later Sucrose => AAV | 1 hr later Sucrose => AAV |
|---|---|---|---|---|---|
| Fluorescence Intensity | 246.3 | 2500.8 | 2356.2 | 2580.3 | 3047 |
| Relativeness | 1.0 | 10.2 | 9.6 | 10.5 | 12.4 |

As the second procedure, the AAV vector and sucrose were mixed in advance, and the mixture was administered to cells immediately (5 minutes or less) after mixing or after allowed to stand at room temperature for 1 hour in such a manner that the amount of AAV3B-CMV-AcGFP was $1×10^8$ vg/well and the final concentration of sucrose was 125 mM. Sucrose (−) indicates a material obtained by mixing the medium in the same amount as that of the sucrose solution with the AAV vector, followed by being allowed to stand at room temperature for 1 hour. In the same manner as the above-described procedure, the GFP expression level was measured 3 days later.

As the results of the experiments, in the cases of the methods in which the AAV vector was mixed with sucrose followed by administration thereof, both of the cases of the administration immediately after mixing and the administration 1 hour after mixing also enhanced the expression by 12 times or more (FIG. 4B).

TABLE 4B

|  |  | Mixing time | |
|---|---|---|---|
|  | Sucrose(−) | Immediately | 1 hr later |
| Fluorescence Intensity | 246.3 | 3002.5 | 3049.8 |
| Relativeness | 1.0 | 12.2 | 12.4 |

As the third procedure, immediately (5 minutes or less) after the administration of $1×10^8$ vg/well of AAV3B-CMV-AcGFP vector, a sucrose (+) medium or sucrose (−) medium was added, and 3 hours later, the whole medium was replaced with a medium having 125 mM of sucrose (+) or no sucrose (−). In the same manner as the above-described procedures, the GFP expression level was measured 3 days later.

As the results of the experiments, in the state where sucrose was present from immediately after the administration of AAV, the expression was enhanced by 4.9 times, and also in the case of adding sucrose 3 hours later (at the period of this time, AAV infection was expected to complete), the expression was enhanced by 2.8 times (FIG. 4C).

TABLE 4C

|  | Sucrose | | |
|---|---|---|---|
|  | (−) => (−) | (−) => (+) | (+) => (+) |
| Fluorescence Intensity | 109.8 | 309.8 | 534.5 |
| Relativeness | 1.0 | 2.8 | 4.9 |

Experiment 5: Expression Enhancing Effects when Using D-Glucose or L-Glucose

Either L-glucose (Sigma), which does not exist in nature and is considered to be not utilized by cells (not incorporated into glycolysis), or D-glucose, which usually exists in nature, was mixed with AAV3B-CMV-AcGFP, and the mixture was allowed to stand at room temperature for 1 hour and then administered to cells in such a manner that the amount of AAV was $1×10^8$ vg/well and the final concentration of each glucose was 132 mM. After cell cultivation for 1, 2 or 3 days in an incubator under 5% $CO_2$ at 37° C., the fluorescence intensity of GFP was measured using the plate reader and comparison thereof was made. As to the cells, $5×10^4$ cells/well of HEK293 cells were seeded on a 96 well Optical bottom plate and used on the next day.

As the results of the experiments, one day after the administration, the expression was enhanced by about 17 times due to adding D-glucose, and the expression was also enhanced by 11 times due to adding L-glucose. It is inferred that it is not because cell metabolism was activated by the mixed sugar but because the sugar was involved in AAV vector infection itself (FIG. 5A).

TABLE 5A

|  | Glucose(−) | D-Glucose | L-Glucose |
|---|---|---|---|
| Fluorescence Intensity | 9.5 | 161.0 | 104.7 |
| Relativeness | 1 | 16.9 | 11.0 |

Meanwhile, the difference in the expression intensity between the D-form and the L-form (D/L) was 1.5 times 1 day later, whereas it was increased to 2.1 times 3 days later. Accordingly, it is inferred that there is possibility that the sugar enhances expression also as a result of enhancing cell activity (FIG. 5B).

TABLE 5B

|  | D-Glucose | L-Glucose | Glucose(−) | D/L ratio |
|---|---|---|---|---|
| Day 1 | 161.0 | 104.7 | 9.5 | 1.5 |
| Day 2 | 1232.5 | 669.2 | 67.5 | 1.8 |
| Day 3 | 2966.3 | 1397.7 | 316.0 | 2.1 |

Experiment 6: Difference in Expression Enhancing Effects Depending on Sucrose Concentrations in Medium AAV3B-CMV-AcGFP was mixed in advance with sucrose at each of various concentrations, and the mixture was allowed to stand at room temperature for 1 hour followed by administration to cells. The final dose of the AAV vector was 1×10$^8$ vg/well, and the final concentration of sucrose was from 80 mM to 160 mM. Regarding sucrose (−), the medium in the same amount as that of the sucrose solution was mixed. In order to prevent cell damage due to a buffer at the time of dilution of sucrose, medium replacement was carried out using a sucrose solution having the same concentration that was prepared by the medium 3 hours after the administration. After cell cultivation for 3 days in an incubator under 5% $CO_2$ at 37° C., the fluorescence intensity of GFP was measured using the plate reader and comparison thereof was made. As to the cells, 5×10$^4$ cells/well of HEK293 cells were seeded on a 96 well Optical bottom plate and used on the next day.

As the results of the experiments, the expression was enhanced by 5 times or more in the case where the sucrose concentration was 80 mM in the medium. The effect was increased in a concentration-dependent manner, and expression was highly enhanced (by about 30 times) in the case where the concentration was 145, 150 or 160 mM. The optimum concentration after 3 days was 150 mM (FIG. 6). When the sucrose concentration was further increased to 187 mM, the cells were damaged and detached, and the GFP intensity was significantly decreased (by about 20%) (data not shown).

TABLE 6

| Sucrose conc. (mM) | 0 | 80 | 90 | 100 | 105 | 110 | 115 | 120 |
|---|---|---|---|---|---|---|---|---|
| Fluorescence Intensity | 192.5 | 1026.0 | 1230.5 | 1568.3 | 1769.3 | 1952.3 | 2351.3 | 2941.0 |
| Relativeness | 1.0 | 5.3 | 6.4 | 8.1 | 9.2 | 10.1 | 12.2 | 15.3 |

| Sucrose conc. (mM) | 125 | 130 | 135 | 140 | 145 | 150 | 160 |
|---|---|---|---|---|---|---|---|
| Fluorescence Intensity | 3626.8 | 4069.0 | 4813.3 | 5620.5 | 5763.8 | 6411.8 | 5922.5 |
| Relativeness | 18.8 | 21.1 | 25.0 | 29.2 | 29.9 | 33.3 | 30.7 |

Experiment 7: Difference in Expression Enhancing Effects Depending on Glucose Concentration in Medium AAV3B-CMV-AcGFP was mixed with glucose at each of various concentrations in advance, and the mixture was allowed to stand at room temperature for 1 hour and then administered to cells. The final dose of AAV was 1×10$^8$ vg/well, and the final concentration of glucose was 40 mM to 200 mM. Regarding glucose (−), the medium in the same amount as that of the glucose solution was mixed. In order to prevent cell damage due to a buffer at the time of dilution of glucose, medium replacement was carried out using a glucose solution having the same concentration that was prepared by the medium 3 hours after the administration. After cell cultivation for 3 days in an incubator under 5% $CO_2$ at 37° C., the fluorescence intensity of GFP was measured using a plate reader and comparison thereof was made. As to the cells, 5×10$^4$ cells/well of HEK293 cells were seeded on a 96 well Optical bottom plate and used on the next day.

As the results of the experiments, the expression was enhanced by 3 times or more when the glucose concentration was 80 mM in the medium. The effect of enhancement was increased in a concentration-dependent manner, and the expression was enhanced by about 60 times when the concentration was 200 mM (FIG. 7).

TABLE 7

| Glucose conc. (mM) | 0 | 40 | 80 | 120 | 132 | 160 | 200 |
|---|---|---|---|---|---|---|---|
| Fluorescence Intensity | 187.8 | 274.0 | 579.8 | 1493.5 | 2050.8 | 5305.5 | 11125.5 |
| Relativeness | 1.0 | 1.5 | 3.1 | 8.0 | 10.9 | 28.3 | 59.3 |

Experiment 8: Expression Enhancing Effects of AAV Using Disaccharides

HEK293 cells ($5\times10^4$ cells/well) were seeded on a 96 well Optical bottom plate, and the next day, the original medium was replaced with a medium containing one of 4 types of disaccharides, that were sucrose, trehalose, maltose and lactose (all from Sigma except for sucrose), at a concentration of 100, 125 or 150 mM. After that, AAV3B-CMV-AcGFP ($1\times10^8$ vg/well) was administered. To a control, the medium in the same amount as that of the sugar solution was added. After cell cultivation for 1, 2, 3 or 6 days in an incubator under 5% $CO_2$ at 37° C., the fluorescence intensity of GFP was measured using a plate reader and comparison thereof was made (FIG. 8A). Further, the images of typical view fields were taken using the fluorescence microscope (Olympus IX83) (FIG. 8B).

As the results of the experiments, 3 days after the administration, the expression was enhanced by 2 to 6 times by using all types of the sugars in a concentration-dependent manner.

TABLE 8-1

|  | No Sugar | Sucrose (mM) | | | Trehalose (mM) | | | Maltose (mM) | | | Lactose (mM) | | |
| --- | --- | --- | --- | --- | --- | --- | --- | --- | --- | --- | --- | --- | --- |
|  |  | 100 | 125 | 150 | 100 | 125 | 150 | 100 | 125 | 150 | 100 | 125 | 150 |
| Fluorescence Intensity | 609.0 | 1312.7 | 1760.5 | 2979.5 | 995.7 | 1249.0 | 1903.7 | 1158.0 | 1833.5 | 3281.8 | 1189.0 | 1880.3 | 3606.8 |
| Relativeness | 1.0 | 2.2 | 2.9 | 4.9 | 1.6 | 2.1 | 3.1 | 1.9 | 3.0 | 5.4 | 2.0 | 3.1 | 5.9 |

When comparison was made for the concentration of 150 mM of the sugars, lactose showed the highest effect. However, since lactose has solubility extremely lower than the other sugars, it may be inappropriate for practical use. In the case of maltose, the expression at day 6 was stronger than others, and there was a difference of transition of expression enhancement between the sugars (FIG. 8C).

TABLE 8-2

|  | Fluorescence Intensity | | | |
| --- | --- | --- | --- | --- |
|  | Day 1 | Day 2 | Day 3 | Day 6 |
| No Sugar | 20.7 | 191.7 | 609.0 | 2006.3 |
| Sucrose | 434.5 | 1657.3 | 2979.5 | 7908.0 |
| Trehalose | 230.7 | 949.8 | 1903.7 | 6490.7 |
| Maltose | 532.7 | 2009.0 | 3281.8 | 13867.8 |
| Lactose | 503.2 | 2097.0 | 3606.8 | 10798.2 |

Experiment 9: Expression Enhancing Effects of AAV Using Monosaccharides

On a 96 well Optical bottom plate, $5\times10^4$ cells/well of HEK293 cells were seeded and AAV3B-CMV-AcGFP was mixed on the next day with one of monosaccharides, including glucose, galactose, fructose or mannose (all from Sigma), at one of two concentrations, and the mixture was allowed to stand at room temperature for 1 hour and then administered to the cells. The final dose of AAV was $1\times10^8$ vg/well, and the sugar concentration was 100 or 200 mM in the medium. To a control, the medium in the same amount as that of the sugar solution was added. After cell cultivation for 3 days in an incubator under 5% $CO_2$ at 37° C., the fluorescence intensity of GFP was measured using the plate reader and comparison thereof was made (FIG. 9A). Further, 3 days after the administration, the images of typical view fields were taken using the fluorescence microscope (Olympus IX83) (FIG. 9B).

As the results of the experiments, among the monosaccharides, i.e., glucose, galactose, fructose and mannose, glucose showed an overwhelmingly high effect of enhancement and in the case of 200 mM of glucose the effect thereof showed 120 times. The effects of fructose and mannose were comparable to that of sucrose. The effect of galactose was lower than those of the other sugars.

TABLE 9

| | Galactose (mM) | | Fructose (mM) | | Mannose (mM) | | Glucose (mM) | | |
|---|---|---|---|---|---|---|---|---|---|
| | 100 | 200 | 100 | 200 | 100 | 200 | 100 | 200 | (−) |
| Fluorescence Intensity | 189.5 | 583.5 | 402.0 | 2378.5 | 400.5 | 2840.3 | 393.0 | 17748.0 | 147.0 |
| Relativeness | 1.3 | 4.0 | 2.7 | 16.2 | 2.7 | 19.3 | 2.7 | 120.7 | 1.0 |

INDUSTRIAL APPLICABILITY

The composition of the present invention can significantly improve the efficiency of gene transfer using a recombinant virus vector. The composition of the present invention can be expected to be utilized as a pharmaceutical for gene therapy.

SEQUENCE LISTING FREE TEXT

SEQ ID NO: 1: amino acid sequence of AAV3A VP1 protein
SEQ ID NO: 2: amino acid sequence of AAV3B VP1 protein
SEQ ID NO: 3: amino acid sequence of yf2AAV9 VP1 protein (Y446F/Y731F mutant)
SEQ ID NO: 4: amino acid sequence of AAV GT4 VP1 protein

---

The invention claimed is:

1. An ex vivo or in vitro method for gene transfer, comprising:
   (a) providing a composition comprising a recombinant adeno-associated virus (AAV) vector and a sugar at a concentration of at least 40 mM; and
   (b) bringing the composition into contact with a culture cell in a medium comprising the sugar at a final concentration of at least 40 mM.

2. The method according to claim 1, wherein the recombinant AAV vector is derived from AAV1, AAV2, AAV3, AAV4, AAV5, AAV6, AAV7, AAV8, AAV9, AAVrh10, AAVrh39, AAVrh43, AAV-B1, AAV-PHP.B or AAV-PHP.eB.

3. The method according to claim 1, wherein the recombinant virus vector comprises a capsid containing a protein having an amino acid sequence of SEQ ID NO: 1, 2, 3 or 4 or an amino acid sequence having at least about 90% identity to the amino acid sequence of SEQ ID NO: 1, 2, 3 or 4.

4. The method according to claim 1, which comprises the sugar at a concentration of from 0.04 to 2 M.

5. The method according to claim 1, wherein the sugar comprises a monosaccharide, a disaccharide or a combination thereof.

6. The method according to claim 5, wherein the monosaccharide comprises at least one selected from glucose, galactose, fructose, mannose or a combination thereof.

7. The method according to claim 4, wherein the monosaccharide comprises at least 60% of the D-form.

8. The composition according to claim 5, wherein the disaccharide comprises at least one selected from the group consisting of sucrose, trehalose, maltose, lactose and a combination thereof.

9. The method according to claim 1, wherein the aqueous medium is water for injection.

10. An in vivo method for gene transfer, comprising:
    (a) providing a composition comprising a recombinant AAV vector and a sugar at a concentration of at least 40 mM;
    (b) increasing the local concentration of the recombinant AAV vector and the sugar in an organ, tissue or a part thereof targeted for gene transfer; and
    (c) bringing the composition into contact with a cell in the organ, tissue or a part thereof comprising the sugar at a final concentration of at least 40 mM.

11. An in vivo method for gene transfer, comprising:
    (a) providing a composition comprising a recombinant AAV vector and a sugar at a concentration of at least 40 mM;
    (b) temporarily stopping blood flow, lymph or cerebrospinal fluid in a target site for gene transfer in a subject using a clamp,
    (c) carrying out substitution, perfusion and/or flushing with a physiological saline, and
    (d) administrating the composition to the target site so that a target cell in the target site contacts with a medium for gene transfer comprising the sugar at a final concentration of at least 40 mM.

12. An in vivo method for gene transfer, comprising:
    (a) providing a composition comprising a recombinant AAV vector and a sugar at a concentration of at least 40 mM;
    (b) administrating to a subject the composition into blood or lymph of the subject with injection or infusion so that a target cell contacts with blood or lymph comprising the sugar at a final concentration of more than 8.5 mM and 10 mM or less.

13. An in vivo method for gene transfer, comprising:
    (a) providing a composition comprising a recombinant AAV vector and a sugar at a concentration of at least 40 mM;
    (b) administrating to a subject the composition intrathecally so that a target cell contacts with cerebrospinal fluid comprising the sugar at a final concentration of at least 40 mM.

* * * * *